(12) United States Patent
Wallach et al.

(10) Patent No.: US 8,092,806 B2
(45) Date of Patent: Jan. 10, 2012

(54) CHIMERIC PROTEINS, THEIR PREPARATION AND PHARMACEUTICAL COMPOSITIONS CONTAINING THEM

(75) Inventors: David Wallach, Rehovot (IL); Elena Appel, Rishon Le Zion (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 51 days.

(21) Appl. No.: 11/911,252

(22) PCT Filed: Apr. 10, 2006

(86) PCT No.: PCT/IL2006/000456
§ 371 (c)(1),
(2), (4) Date: Jun. 25, 2008

(87) PCT Pub. No.: WO2006/109303
PCT Pub. Date: Oct. 19, 2006

(65) Prior Publication Data
US 2008/0287356 A1   Nov. 20, 2008

(30) Foreign Application Priority Data
Apr. 11, 2005   (IL) .......................................... 167959

(51) Int. Cl.
*A61K 39/00* (2006.01)
*A61K 38/18* (2006.01)
(52) U.S. Cl. ................. 424/185.1; 424/192.1; 435/69.7; 514/8.4
(58) Field of Classification Search .................. None
See application file for complete search history.

(56) References Cited

U.S. PATENT DOCUMENTS
2004/0208889 A1* 10/2004 Sutton et al. ............... 424/190.1

FOREIGN PATENT DOCUMENTS
WO    WO/98/56817    * 12/1998

OTHER PUBLICATIONS

Navarro et al., Functions of the Yersinia effector proteins in inhibiting host immune responses. Current Opinion in Microbiology 8, 21-27, 2005—available on line Jan. 7, 2005.*
Smyth et al., Role of TNF in Lymphocyte-Mediated Cytotoxicity—Microscopy Research and Technique, 50, 196-208, 2000.*
Siegall et al., Functional Analysis of Domains II, Ib, and III of Pseudomonas Exotoxin—J. Biol. Chem. 264, 14256-14261, 1989.*
Terlizzese et al., In Vitro Comparison of Inhibiting Ability of Soluble TNF Receptor p75 (TBPII) vs. Soluble TNF Receptor p55 (TBPI) Against TNF-α and TNF-β- J. Interferon Cytokine Res. 16, 1047-1053, 1996.*
Ruckdeschel et al., Arginine-143 of *Yersinia enterocolitica* YopP Crucially Determines Isotype-Related NF-KB Suppression and Apoptosis Induction in Macrophages—Infection and Immunity, 69, 7652-7662, 2001.*
Taupiac et al., A deletion within the translocation domain of Pseudomonas exotoxin A enhances translocation efficiency and cytotoxicity concomitantly—Mol. Microbiol. 31-1385-1393, 1999.*
Gordon et al., Proteolytic Activation of Bacterial Toxins by Eukaryotic Cells Is Performed by Furin and by Additional Cellular Proteases—Infection and Immunity, 63, 82-87, 1995.*
Bonifacio and Traub, Annu. Rev. Biochem. 72:395-447(2003).
Xu et al., "A Comparison of Noninternalizing (Herkinorin) and Internalizing (DAMGO)m-Opioid Agonists on Cellular Markers Related to Opioid Tolerance and Dependence", Synapse 61:166-175 (2007).
Smalley et al., "Ligand internalization and recycling by human recombinant somatostatin type 4 (h sst4) receptors expressed in CHO-K1 cells", British Journal of Pharmacology 132:1102-1110 (2001).
Vogel, WF, "Ligand-induced shedding of discoidin domain receptor 1", FEBS Lett. 514:175-180 (2002).
Hakozaki et al., "Receptor Activator of NF-kB (RANK) Ligand Induces Ectodomain Shedding of RANK in Murine RAW264.7 Macrophages", J. Immunol. 184:2442-2448 (2010).

* cited by examiner

*Primary Examiner* — Elly-Gerald Stoica
(74) *Attorney, Agent, or Firm* — Browdy and Neimark, PLLC

(57) ABSTRACT

The present invention relates to a chimeric protein comprising a cell-targeting agent and a *Yersinia* outer protein, connected by a translocating polypeptide. The invention further relates to the preparation and use of such chimeric protein.

18 Claims, 14 Drawing Sheets

Fig. 1C

Figure 1A:
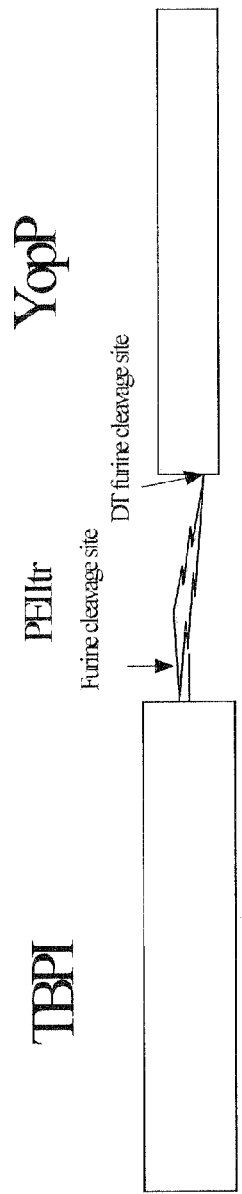

ATGGATAGTGTGTGTCCCAAGGAAAATATATCCACCCTCAAAATAATTCGATTTGCTGTACCAAGTGCCACAAAGGAAC
CTACTTGTACAATGACTGTCCAGGCCCGGGCAGGATACGGACTGCCAGGGAGTGTGAGAGCGCTCCCTTCACCGCTTCAG
AAACCACCTCAGACACTGCCTCAGCTGCTCCAAATGCCGAAAGGAAATGGGTCAGGTGGAGATCTCTTCTTGCACAGTG
GACCGGGACACCGTGTGTGGCTGCAGGAAGAACCAGTACCGGCATTATTGGAGTGAAAACCTTTTCCAGTGCTTCAATTG
CAGCCTCTGCCTCAATGGACCGTGTCTCCTGTAGTAACTGTAAGAAAAAGCCTGGAGTGCACGAAGTTGTGCCTACCCAGATT
TTCTAAGAGAAACGAGTGTGTCTCCTGTAGTAACTGTAAGAAAAAGCCTGGAGTGCACGAAGTTGTGCCTACCCAGATT
GAGAATAAAGCTTCCGAGGTCCCAGGCGGCAGCCTGGCGCGCGCGCTGCTGCTGCCGCGCGCCTGGAGCAGTGCCGGCTTGCCCACCTGCCGCTGGA
GACTTTCACCCGTCATCGCCGGCTGTCGTGGAACCAGTCGACCAGTTGGGAACAACCAGTGCCGTCTGCCCTGACCCTGGCCGCCCTGGCCCGGTGCGGGCGC
TCTACCTGGCGGCGAAGCGATCCGCGAGCAGCCCGGAGCAGTGAGAAGAATGATTGGGCCAATATCACAACACAGTGGAAACAGCCCCGTG
GACCTGGGCGCAGGGCACCGGCAACGACCAGTTCTTAATCAGTCACGTACAGATGTAAAAGTCATGCCCGATTGGTAACTCAGGCGAACAA
CGTCCGGCAGGGCCACCGGCAACGACCAGTTCTTAATCAGTCACGTACAGATGTAAAAGTCATGCCCGATTGGTAACTCAGGCGAACAA
GCGGATGGATCCTGGTTCCATAAAATTATTCGTTTACATCTCCACTGGACCTTTCGATAGAATAAAAACGTCATAGAAAATG
TAAATATCCTGAAATGAATCTTAATTTGTTTACATCTCCACTGGACCTTTCGATAGAATAAAAACGTCATAGAAAATG
GAGTTGGATCTTCCCGCTTCATATTGTTTGAACCAGCAAACTTTAACAGTATGGGGCCAGCAGTACATTCAGTGTAATTGATTACAAACATATAAAT
GGGAAAACATCTCTGATATTGTTTGAACCAGCAAACTTTAACAGTATGGGGCCAGCAGTACATTCAGTGTAATTGATTACAAACATATAAAT
GGCCATTGAACGTTATCAATTACCTGATTGCCATTTCTCCATGTGGAAATGGATATTCAGCGAAGCTCATCTGAATGTG
GTATTTTAGTTTGGCACTGGCAAAAATCCTTTACCCCACGATAAGTTGGATCCGTATCTCCCGGTAACTTTTTACAAAACATAC
GGTATATTAAGTGATGGTGAAATGTCTTAATGAATATTTAAATACTAACCCGCAGGAGTTGGTACTGTTGTTAACAAAAAATGAAA
TCAAGGTAAAAAACGTCTTAATGAATATTTAAATACTAACCCGCAGGAGTTGGTACTGTTGTTAACAAAAAATGAAA
CCATCTTTAATAGGTTTGATAACAATAAATCCATTATAGATGAAAGGAATTATCAGTTTCGGCACACATAAAAGAGAATA
GCTGAATATAAAACACTTCTCAAAGTA

Fig. 2 ggcggcagcctggccgctgaccgctgaccaggttgccacctgccgctggagactttcacccgtcatcgcca
gccgcgggctgggaacaactgagcagtgcgctatccgtgcagcggtgcccctactggcggc
gcggctgtcgtggaaccaggtcgacaggtgatccgcaacgccctggccagcgccggcgggcgacct
gggcgaagcgatccgcagccggagcaggcccgtctggccctgacccctggccgctggccgagagcgagc
gcttcgtccggcagggcaccggcaacgac

Fig. 3

GGSLAALTAHQACHLPLETFTRHRQPRGWEQLEQCGYPVQRLVALYLAARLSWNQVDQVIRNALASPGSGG
DLGEAIREQPEQARLALTLAAAESERFVRQGTGND

SEQUENCE LISTING

```
<160> NUMBER OF SEQ ID NOS: 9

<210> SEQ ID NO 1
<211> LENGTH: 1707
<212> TYPE: DNA
<213> ORGANISM: Artificial
<220> FEATURE:
<223> OTHER INFORMATION: synthetic

<400> SEQUENCE: 1
atggatagtg tgtgtcccca aggaaaatat atccaccctc aaaataattc gatttgctgt      60
accaagtgcc acaaaggaac ctacttgtac aatgactgtc caggcccggg gcaggatacg     120
gactgcaggg agtgtgagag cggctccttc accgcttcag aaaaccacct cagacactgc     180
ctcagctgct ccaaatgccg aaaggaaatg ggtcaggtgg agatctcttc ttgcacagtg     240
gaccgggaca ccgtgtgtgg ctgcaggaag aaccagtacc ggcattattg gagtgaaaac     300
cttttccagt gcttcaattg cagcctctgc ctcaatggga ccgtgcacct ctcctgccag     360
gagaaacaga acaccgtgtg cacctgccat gcaggtttct ttctaagaga aaacgagtgt     420
gtctcctgta gtaactgtaa gaaaagcctg gagtgcacga agttgtgcct accccagatt     480
gagaataaag cttccggagg tcccgagggc ggcagcctgg ccgcgctgac cgcgcaccag     540
gcttgccacc tgccgctgga gactttcacc cgtcatcgcc agccgcgcgg ctgggaacaa     600
ctggagcagt gcggctatcc ggtgcagcgg ctggtcgccc tctacctggc ggcgcggctg     660
tcgtggaacc aggtcgacca ggtgatccgc aacgccctgg ccagcccggg cagcggcggc     720
gacctgggcg aagcgatccg cgagcagccg gagcaagccc gtctggccct gaccctggcc     780
gccgccgaga gcgagcgctt cgtccggcag ggcaccggca acgaccccgg gagagtgaga     840
agaatgattg gccaatatc acaaataaac agccccggtg gcttatcaga aaaagagacc     900
agttctttaa tcagtaatga agagcttaaa aatatcataa cacagttgga aactgatata     960
gcggatggat cctggttcca taaaaattat tcacgtacag atgtaaaagt catgcccgca    1020
ttggtaactc aggcgaacaa taaatatcct gaaatgaatc ttaattttgt tacatctcca    1080
ctggaccttt cgatagaaat aaaaaacgtc atagaaaatg gagttggatc ttcccgcttc    1140
ataattaaca tggggggaaga tggaatacat ttcagtgtaa ttgattacaa acatataaat    1200
gggaaaacat ctctgatatt gtttgaacca gcaaacttta acagtatggg gccagcgatg    1260
ctggcaataa gggcaaaaac ggccattgaa cgttatcaat tacctgattg ccatttctcc    1320
atggtggaaa tggatattca gcgaagctca tctgaatgtg gtatttttag tttggcactg    1380
gcaaaaaaac tttacaccga gagagataac ctgttgaaaa tacatgaaga taatataaaa    1440
ggtatattaa gtgatggtga aaatcctta ccccacgata agttggatcc gtatctcccg    1500
gtaacttttt acaaacatac tcaaggtaaa aaacgtctta atgaatattt aaatactaac    1560
```

```
ccgcagggag ttggtactgt tgttaacaaa aaaaatgaaa ccatctttaa taggtttgat    1620
aacaataaat ccattataga tggaaaggaa ttatcagttt cggcacataa aaagagaata    1680
gctgaatata aaacacttct caaagta                                       1707
```

```
<210> SEQ ID NO 2
<211> LENGTH: 318
<212> TYPE: DNA
<213> ORGANISM: Artificial
<220> FEATURE:
<223> OTHER INFORMATION: synthetic

<400> SEQUENCE: 2
ggcggcagcc tggccgcgct gaccgcgcac caggcttgcc acctgccgct ggagactttc      60
acccgtcatc gccagccgcg cggctgggaa caactggagc agtgcggcta tccggtgcag     120
cggctggtcg ccctctacct ggcggcgcgg ctgtcgtgga accaggtcga ccaggtgatc     180
cgcaacgccc tggccagccc cggcagcggc ggcgacctgg cgaagcgat ccgcgagcag      240 ccggagcagg cccgtctggc cctgaccctg gccgccgccg agagcgagcg cttcgtccgg     300
cagggcaccg gcaacgac                                                  318
```

```
<210> SEQ ID NO 3
<211> LENGTH: 106
<212> TYPE: PRT
<213> ORGANISM: Artificial
<220> FEATURE:
<223> OTHER INFORMATION: synthetic

<400> SEQUENCE: 3

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp
            100                 105
```

```
<210> SEQ ID NO 4
<211> LENGTH: 29
<212> TYPE: DNA
<213> ORGANISM: Artificial
<220> FEATURE:
<223> OTHER INFORMATION: synthetic

<400> SEQUENCE: 4
catcatatgg atagtgtgtg tccccaagg                                       29
```

```
<210> SEQ ID NO 5
<211> LENGTH: 32
<212> TYPE: DNA
<213> ORGANISM: Artificial
<220> FEATURE:
<223> OTHER INFORMATION: synthetic
```

-continued

```
<400> SEQUENCE: 5
aggaagcttt attctcaatc tggggtaggc ac                           32

<210> SEQ ID NO 6
<211> LENGTH: 52
<212> TYPE: DNA
<213> ORGANISM: Artificial
<220> FEATURE:
<223> OTHER INFORMATION: synthetic

<400> SEQUENCE: 6
aattaaagct tccggaggtc ccgagggcgg cagcctggcc gcgctgaccg cg     52

<210> SEQ ID NO 7
<211> LENGTH: 38
<212> TYPE: DNA
<213> ORGANISM: Artificial
<220> FEATURE:
<223> OTHER INFORMATION: synthetic

<400> SEQUENCE: 7
gtgaattctt acccggggtc gttgccggtg ccctgccg                     38

<210> SEQ ID NO 8
<211> LENGTH: 50
<212> TYPE: DNA
<213> ORGANISM: Artificial
<220> FEATURE:
<223> OTHER INFORMATION: synthetic

<400> SEQUENCE: 8
atcccgggag agtgagaaga atgattgggc caatatcaca aataaacagc        50

<210> SEQ ID NO 9
<211> LENGTH: 38
<212> TYPE: DNA
<213> ORGANISM: Artificial
<220> FEATURE:
<223> OTHER INFORMATION: synthetic

<400> SEQUENCE: 9
cagaattctt atactttgag aagtgtttta tattcagc                     38
```

CHIMERIC PROTEINS, THEIR PREPARATION AND PHARMACEUTICAL COMPOSITIONS CONTAINING THEM

FIELD OF THE INVENTION

The present invention relates to a chimeric protein comprising a cell-targeting agent and a *Yersinia* outer protein, connected by a translocating polypeptide. The invention further relates to the preparation and use of such chimeric protein.

BACKGROUND OF THE INVENTION

Cytokines of the tumor necrosis factor (TNF) family provide a unique point of view of biological regulation. These cytokines and their receptors are expressed in almost all cells and trigger a wide range of different, in part contrasting, cellular activities (Wallach et al., 1999, Locksley et al., 2001, and Wallach et al. 2000). They help to regulate practically every aspect of immune defense, as well as certain developmental processes. All of these activities are mediated by a unique set of apparently few signaling proteins, which are shared by the different receptors (Wallach et al., 1999).

Cytokines normally serve to enhance defense. However, when acting in excess, they may cause great damage, comparable to that which pathogens can cause. In fact, in many diseases, unwarranted effects of cytokines constitute a major pathogenic cause.

Cytokines of the TNF family regulate a wide range of different immune defense mechanisms, both of the innate and the adaptive types. Excessive function of several of them, including TNF, the Fas ligand, CD40 ligand and others have been implicated in the pathology of various diseases. There is, in particular, extensive evidence for a major pathological role of TNF in a wide range of diseases: infectious diseases such as malaria and sepsis, autoimmune diseases such as rheumatoid arthritis, inflammatory bowel diseases and psoriasis, and certain types of cancer. Indeed, blocking TNF action by agents such as anti-TNF antibodies or soluble TNF receptors was found to provide therapy at such situations (Beutler, 1999, Kollias et al., 1999 and Reimold, 2003). In some pathological situations, including rheumatoid arthritis and Crohn's disease, a rather significant proportion of the patients respond favorably to anti-TNF therapy. There are, however, also patients with such diseases that respond rather poorly to these agents, raising the need to find additional approaches for therapy (Andreakos et al., 2002).

Unlike many other cytokines that act solely as soluble proteins following their secretion by the cytokine-producing cell, the ligands of the TNF family are produced as cell-bound type II transmembrane proteins (with the exception of lymphotoxin which is produced as a soluble secreted protein). They can exert their effects in this form, affecting only cells that are located adjacently to the ligand-producing cell (juxtacrine regulation). Most of them are also shed, forming soluble molecules that circulate. Part of those soluble ligands, for example TNF, are capable of acting as soluble cytokines, serving as paracrine regulators (affecting cells located relatively close to the ligand producing-cells) and endocrine regulators (affecting remote cells). Some ligands of the TNF family, for example the Fas ligand, do not act effectively in their shed form and may in that form even serve as antagonist to the cell-bound form (Wallach et al., 1999 and Locksley et al., 2001).

The occurrence of ligands of the TNF family on the surface of the cells producing them provides a potential means for specific targeting of these ligand-producing cells. Such means can allow selective killing of the ligand-producing cells at situations where the ligand plays a pathogenic role.

In several respects, destruction of cells producing a cytokine may turn to provide even better defense against the pathogenic effects of this cytokine than just direct blocking of the function of the cytokine molecules. Destruction of the cytokine-producing cell prevents further synthesis of the cytokines and thus is likely to provide more durable protection than that obtained by just blocking the effect of the cytokine molecules that had been already synthesized.

Cells producing a cytokine often produce simultaneously some other cytokines that together serve to elicit a particular type of immune response. Well-known examples are the Th1- and Th2-type T lymphocytes, that produce distinct groups of cytokines, each serving to elicit a different type of immune defense (Jankovic et al., 2001). Destroying cells producing a cytokine may thus, besides arrest of the synthesis of that particular cytokine, also result in arrest of synthesis of several other cytokines that assist the former in its pathogenic effects.

While blocking circulating cytokines affects the whole body, killing cytokine-producing cells or attenuation of cytokine production can be restricted to a particular site in the body where these cells reside, thus allowing abolition of the cytokine deleterious effects at that particular site, while maintaining beneficial effects of the cytokine at other sites.

Studies of the effect of anti-TNF therapy in Crohn's disease suggest that killing of TNF-producing cells may, in some pathological situations, indeed provide more effective therapy than that obtained by just blocking TNF. Therapeutic effects of anti-TNF antibodies in this disease were found to correlate with early induction of death of the TNF-producing cells by the antibodies (Lugering et al., 2001, Van Deventer, 2001, and Van den Brande et al., 2003).

TNF-$\alpha$ is expressed by activated monocytes, macrophages and CD8+T cells. These cells present membrane-anchored TNF-$\alpha$ as a key component in their cytolytic pathway. In the following diseases activated macrophages are suspected to be involved in their pathology: septic shock, rheumatoid arthritis, ankylosing spondylitis and psoriatic arthritis (Singh and Suruchi, 2004), psoriasis (Asadullah et al., 2002), amyotrophic lateral sclerosis (Ghezzi et al., 1998), insulin-dependent diabetes mellitus (Kagi et al., 1999), graft-versus-host disease (Hongo et al., 2004), and sickle cell anemia (Belcher et al., 2000). In the following diseases activated CD8+T cells are suspected to be involved in their pathology: systemic lupus erythematosus (Pacheco et al., 2002), reactive arthritis and other autoimmune diseases (Mittler, 2004). Sometimes, activated CD8+T is detrimental to a specific organ. For example, extensive hepatocyte apoptosis which occurs during liver inflammation, is induced following infiltration of activated CD8+T cells to the liver.

Chimeric molecules comprised of a cytotoxin linked to a targeting molecule that binds to a cell-surface constituent can serve as potent cell-killing agents. Choosing a targeting moiety that recognizes a cell-type specific surface constituent can allow applying such cytotoxic chimera for selective destruction of specific cells in vivo. For example, chimeric fusion proteins comprised of antibodies against cancer-specific epitopes fused to *Pseudomonas* exotoxin (PE) or to Diphtheria toxin (DT) can specifically target and kill cancer cells. Such anti-cancer effects have also been obtained with chimera in which the toxins have been fused to hormones or ligands such as IL-2, IL-4 or IL-13, whose receptors are prevalent in certain tumors. Likewise, cytotoxin-containing chimera were designed to be targeted to pathogen-afflicted cells. For example, HIV-infected cells can be selectively destroyed using immunotoxins comprised of an anti-gp120 antibody directed to the conserved CD4 binding site of gp120, or CD4, attached to a *Pseudomonas* exotoxin (Brinkmann and Pastan, 1995, Pastan and Kreitman, 1998 and Pastan, 2003).

One kind of possible agents for targeting cytotoxins or other modulating agents to cells that express ligands of the TNF family are antibodies against these ligands. Indeed, antibodies against the CD40 ligand have been applied to target a toxin to CD40 ligand producing cells (EP 1005372).

U.S. Provisional Application No. 60/582,827 discloses a chimeric protein (TBP-PE38) comprising the extracellular portion of the p55 TNF receptor (TBP-1) attached to the *Pseudomonas aeruginosa* exotoxin translocating and ADP-rybosilating domains (PE38 or PE I-II). It was shown that TBP-PE38 binds epithelial cells overexpressing surface TNF and induces cytotoxicity in such cells.

A variety of bacterial toxins specifically bind to receptors on the cell surface and are internalized via receptor-mediated endocytosis. In general, receptor-mediated endocytosis allows the selective up-take of extracellular proteins (e.g. receptors) and small particles (e.g. ligands) (Molecular cell biology Darnell Lodish and Baltimore). Typically, after binding of a particle to a receptor on the plasma membrane, the receptor-ligand complex is internalized in a clathrin-coated pit that pinches off to become a clathrin-coated vesicle. Then, the clathrin coat depolymerizes to triskelions, resulting in uncoated vesicle, often called endosome. The endosome fuses with an uncoupling vesicle called CURL (compartment uncoupling receptors and ligands), that is characterized by internal pH of about 5.0. The low pH causes the particles to dissociate from the receptor. A receptor-rich region buds off to form a separate vesicle that recycles the receptor back to the plasma membrane.

Proteins internalized by receptor-mediated endocytosis undergo various fates. For example, they can be transferred to the lysosomes, where they are destroyed, they may be minimally processed and remain in the cells, or in other cases the endocytosed material may pass all the way through the cell membranes and exocytosed, or secreted from the plasma membrane at the opposite site.

*Pseudomonas* exotoxin A (PE) binds and enters cells via a α2-macroglobulin receptor/low density lipoprotein receptor-related protein. Following internalization, PE is proteolitically processed in the endosome by a furin-like protease, reduced to a 38 kDa active fragment (PE-38) and such fragment is translocated to the cytosol where it ADP ribosylates elongation factor 2 causing protein synthesis inhibition.

Both proteolytic processing of PE (carried out in the endosome or in the endoplasmic reticulum by furin-like proteases) and translocation of PE-38 to the cytosol are necessary for effective cell toxicity. Domain I of PE (FIG. 1) includes the cell-binding activity, domain II the translocating activity, and domain III the ADP-rybosylating activity. Each one of these domains is comprised of structural units which can be independently refolded. The translocating domain (PEII) contains six consecutive a-helices (A-F). Deletion mapping studies based on the primary structure of the protein showed that the amino-terminal segment encompassing the A and B helices are required for PE translocation (Siegall et al., 1989). At the carboxyl-terminal end, some residues within the E helix were found to be critical, whereas other residues and the entire F helix could be deleted without apparent loss of translocation activity. Moreover, deletion of the last α-helix (F) both enhanced translocation activity and cytotoxicity of PE (Taupiac et al., 1999).

Although there is evidence that the portion of PE exotoxin including PE I-II is capable of translocating barnase, a bacterial enzyme, from the endosome to the cytoplasm of eukaryotic cells (Prior et al., 1996), the translocating activity of domain II flanked by heterologous proteins was not reported nor demonstrated.

*Pseudomonas* exotoxin and diphtheria toxin are powerful cytotoxic agents. *Pseudomonas* exotoxin and diphtheria toxin inhibit protein synthesis affecting the entire cellular metabolism in a wide variety of cells. In contrast, other type of bacterial toxins are known which regulate specific metabolic pathways. For example, each one of the six *Yersinia*'s outer protein (Yop) toxins modulates specific signaling pathways.

*Yersinia pestis* is the causative agent of bubonic plague. *Yersinia pestis* is responsible for three human pandemics: the Justinian plague (VI-VIII centuries), the Black Death and the modern plague. *Yersinia enterocolitica* and *Yersinia pseudotuberculosis* are food-born pathogens, which cause gastroenteritis. The pathogenicity of *Yersinia* results from its ability to overcome the immune defense of the mammalian host.

*Yersinia*'s outer protein P (YopP) is a toxin produced by *Y. enterocolitica*. YopP is essential for the establishment of systemic infection in mice and inhibits production of TNF-α and triggers apoptosis in infected macrophages (Cornelis, Nature 2001). Cytosolic delivery of YopP, which involves translocation across the bacterial double membrane envelope and the host cell membrane, is triggered by an activated protein secretion machinery (type III protein secretion system), which is activated upon host-cell contact. Such protein secretion machinery is absolutely needed for delivery of YopP to the cytosol.

YopP is thought to activate apoptosis through one of two routes, either by activating of BID/caspase 8 pathway and preventing the release of anti-apoptotic factors, or through a less 'direct' pathway involving inhibition of NF-kB. YopP prevents phosphorylation of the NF-kB inhibitor by IKK, and therefore inhibits migration of NF-kB to the nucleus. YopP also causes inhibition of the mitogen-activated protein kinase (MAPK) signaling pathway by inhibiting the upstream MAPK kinases (MEKs). As a result of these inhibitory actions of YopP, transcription activators such as the cAMP-response-element-binding protein (CREB) and activating transcription factor (ATF)-1, as well as NF-kB, cannot stimulate the transcription of genes that are involved in the synthesis of adhesion molecules and pro-inflammatory cytokines such as TNF-α (Orth et al. 1999, Orth, 2002 and Palmer et al., 1999).

YopP seems to be a protease, possibly of the de-SUMOylating family (where SUMO stands for 'small ubiquitin-related modifier'). The predicted secondary structure of YopP is similar to that of cystein protease from adenovirus (AVP). Mutations in catalytic triad (His109, Glu128 and Cys 172 in YopP) disable YopP to inhibit either the MAPK or the NF-kB pathway.

SUMMARY OF THE INVENTION

The invention relates to a chimeric protein comprising the amino acid sequence of a cell-specific targeting agent and the amino acid sequence of a *Yersinia* outer protein (Yop) connected by a polypeptide enabling translocation of the chimeric protein, or of a fragment thereof, from the endosome to the cytosol of a target cell.

In one embodiment of the present invention, the cell-specific targeting agent of the chimeric protein is the extracellular portion of a receptor of a ligand expressed on the surface of the target cell. For example the extracellular portion of the receptor of TNF/NGF ligand, such as TNF binding protein 1 (TBP-1) or TNF binding protein 2 (TBP-2).

In another embodiment of the invention, the Yop in the chimeric protein of the present invention is YopP, or YopP which has reduced or non-apoptotic activity such as YopP serogroups O: 3, O: 9 and O: 8 mutated in the Arginine-143 residue.

Figure 4:
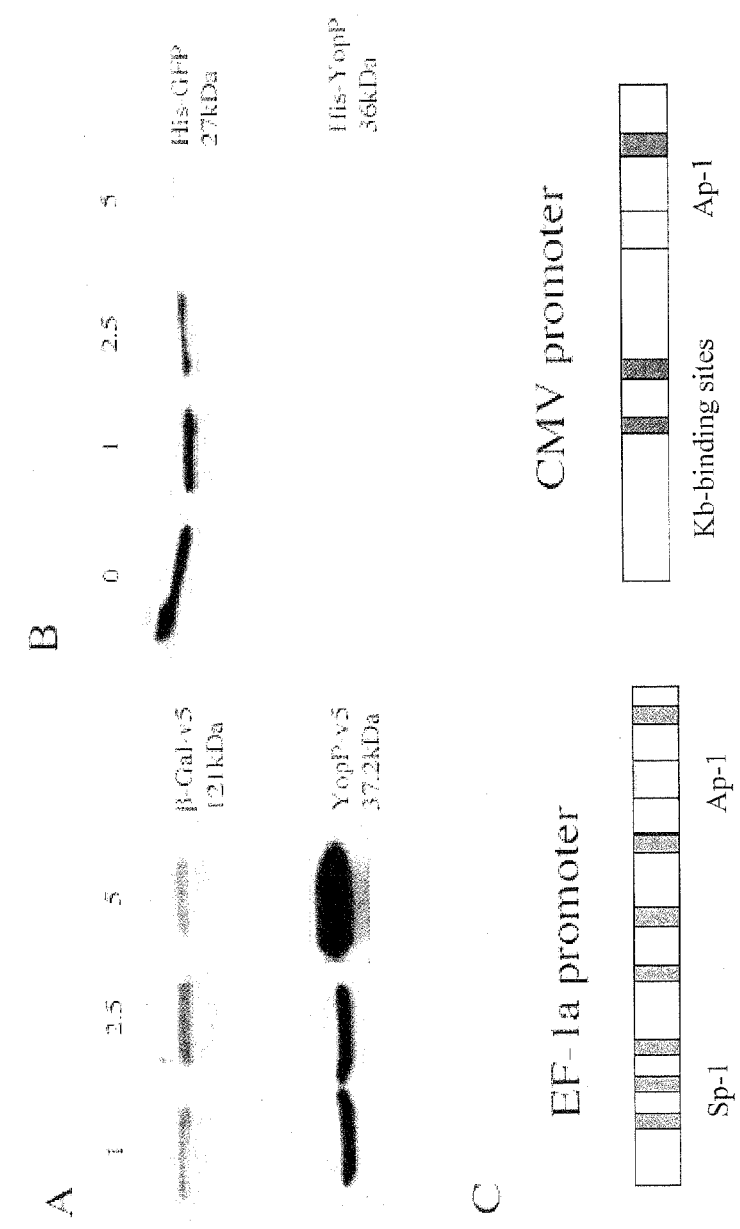

In a further embodiment of the invention, the polypeptide enabling translocation of the chimeric protein of the present invention includes the *Pseudomonas* exotoxin translocation domain or a fragment thereof, such as a translocation domain which is deficient in the last a-helix domain (F) or the translocation domain, herein designated PEIItr, corresponding to the amino acid sequence of *Pseudomonas aeruginosa* exotoxin in FIG. 3 (SEQ ID NO: 3).

In a still further embodiment of the invention, the chimeric protein of the present invention, comprises one or two furine cleavage sites. More specifically, one furin cleavage site, such as that of PE exotoxin, is located at the N-terminus of said polypeptide enabling translocation, while the other furine cleavage site, such as that of the Difteria toxin (e.g. RVRR), is located at the N-terminus of said Yop protein.

In a still further embodiment, the chimeric protein of the present invention consists of TBP-1 the translocation domain fragment of *Pseudomonas aeruginosa* exotoxin PEIItr, the furine cleavage site DT, and YopP, herein designated TBP-YopP, or a mutein, variant, fusion protein, functional derivative, fragment or salt thereof.

In one aspect of the invention, the cell target of the chimeric protein of the invention is a lymphoid cell such as a macrophage or monocyte.

In another aspect of the invention, the cell target of the chimeric protein of the invention is an epithelial cell.

In a further embodiment, the invention provides a DNA sequence encoding said chimeric protein, which may further encode a signal peptide for secretion in eukaryotic cells.

In another further embodiment, the invention provides an expression vector comprising said DNA sequence, and optionally, the DNA is functionally linked to a promoter having an activity, which is independent of NF-kB, such as EF-1α promoter.

In another further embodiment, the invention provides a host cell, such as a prokaryotic or eukaryotic cell such as HeLa, CHO, HEK 293, Yeast, and insect cells comprising said expression vector.

In one aspect of the invention, it is provided a method of producing said chimeric protein, comprising culturing said host cell and isolating said chimeric protein produced.

In another aspect of the invention, a pharmaceutical composition comprising said chimeric protein and a pharmaceutically acceptable carrier is provided.

In a further aspect, the invention provides the use of said chimeric protein in the manufacture of a medicament for treatment of a disease, wherein activity of a ligand of the TNF/NGF receptor, such as TNF, is involved in the pathogenesis or the course of the disease. Example of said diseases are, malaria, sepsis, rheumatoid arthritis, psoriasis, inflammatory bowel disease, and cancer.

In one embodiment, the invention relates to the use said chimeric protein in the manufacture of a medicament for treatment of a disease, wherein activated macrophages or monocytes are involved in the pathogenesis or in the course of the disease. Examples of said diseases are septic shock, rheumatoid arthritis ankylosing spondylitis, psoriasis, amyotrophic lateral sclerosis, insulin-dependent diabetes mellitus, graft-versus-host disease, and sickle cell anemia.

In a further embodiment, the invention relates to the use of said chimeric protein, in the manufacture of a medicament for treatment of a disease, wherein NF-kB activation is involved in the pathogenesis or in the course of the disease and preferably, when NF-kB activation in the disease is induced by NIK via the canonical pathway.

In one aspect, the invention provides a method for the treatment of a disease in which the ligand of the TNF/NGF receptor, such as TNF, is involved in the pathogenesis or in the course of said disease comprising administering to a subject in need a therapeutically effective amount of said chimeric protein.

In one embodiment, the invention provides a method for the treatment of a disease in which activated macrophages or monocytes are involved in the pathogenesis or in the course of said disease, comprising administering to a subject in need a therapeutically effective amount of said chimeric protein.

In a further embodiment, the invention provides a method for the treatment of a disease in which NF-kB activation is involved in the pathogenesis or the in course of said disease, and preferably wherein the NF-kB activation is induced by NIK via the canonical pathway, comprising administering to a subject in need a therapeutically effective amount of said chimeric protein.

In a still further embodiment, the invention provides a method of reducing abnormal expression of a ligand, such as TNF, on the cell surface in a target cell, such as a monocytic or macrophage cell, the method comprising exposing the target cell to a chimeric protein comprising the extracellular portion of a receptor of the ligand expressed on the surface of the target cell, such as TBP-1, and Yop connected by a polypeptide enabling translocation of the chimeric protein from the endosome to the cytosol of the cell, such as PEIItr or of a fragment thereof.

In a further embodiment, the cell is exposed to said chimeric protein in vitro.

In another further embodiment, the cell is exposed to said chimeric protein in vitro.

BRIEF DESCRIPTION OF THE FIGURES

FIGS. 1A-B show schematic representations of TBP-YopP chimeric protein (FIG. 1A), and of *Pseudomonas* exotoxin (PE) (FIG. 1B). TBP-1-TNF-binding protein I; PEIItr-truncated domain II of *Pseudomonas* exotoxin; DT *Diphtheria* toxin furine cleavage site; YopP—*Yersinia* outer protein P. FIG. 1C shows the DNA sequence encoding TBP-YopP chimeric protein (SEQ ID NO: 1).

FIG. 2 shows the DNA sequence of the fragment encoding truncated domain II of *Pseudomonas* exotoxin, PEIItr (SEQ ID NO: 2).

FIG. 3 shows the amino acid sequence of PEIItr (SEQ ID NO: 3).

FIGS. 4A-4C show recombinant expression of YopP in HEK293 cells (human embryonic kidney cells, ATCC number CRL-1573) harboring vectors encoding YopP and a reporter gene, both genes controlled by the EF1-α (FIG. 4A) or CMV (FIG. 4B) promoters. Vectors encoding YopP or β-galactosidase (bGal), both tagged to v5 and controlled by the EF1-α promoter (in the vector pEF6. Invitrogen) were co-transfected in 293 cells (FIG. 4A). 48 hours post transfection, the cells were lysed and subjected to Western blot analysis using anti v5 for detection. 1, 2.5 and 5 μg of YopP-v5/EF6, and 0.1 μg β-Gal/EF6 plasmid was used for transfection. Vectors encoding YopP or green fluorescent protein (GFP), both tagged to His-T7 and controlled by the CMV promoter (in the vector pcDNA3-HisA, Invitrogen) were co-transfected in 293 cells (FIG. 4B). 48 hours post transfection, the cells were lysed and subjected to Western blot analysis using anti T7 for detection. 1, 2.5 and 5 µg of His-YopP/pcDNA3-HisA and 0.1 µg His-GFP/pcDNA3-HisA plasmid was used for transfection. FIG. 4C. shows a schematic representation of the main transcription factor binding sites of EF-1α and CMV promoters. It was observed that the expression of YopP from CMV promoter, which may be repressed in the absence of activated NF-κB, is under detectable level (FIG. 4B), but NF-κB inhibiting activity of YopP is observed, as increasing amounts of YopP expression vector inhibits expression of GFP from the CMV promoter. The EF-1α promoter, which is independent on NF-κB activity, is more appropriate than the CMV promoter for the expression of YopP, and expression of the reporter gene from this promoter is not affected by YopP (FIG. 4A). In all further experiments with eukaryotic cells, YopP or its fusion derivatives are expressed under the control of EF-1α promoter.

Figure 5:
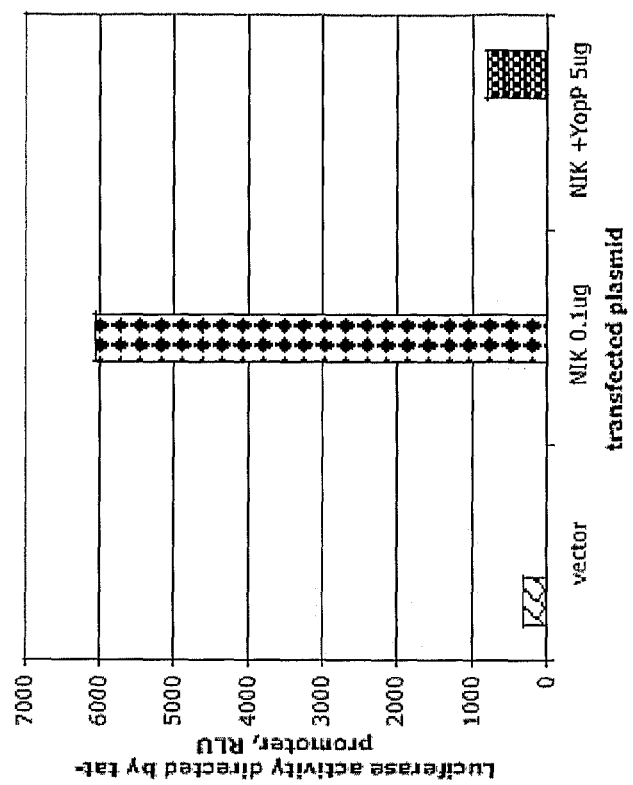
Figure 5:
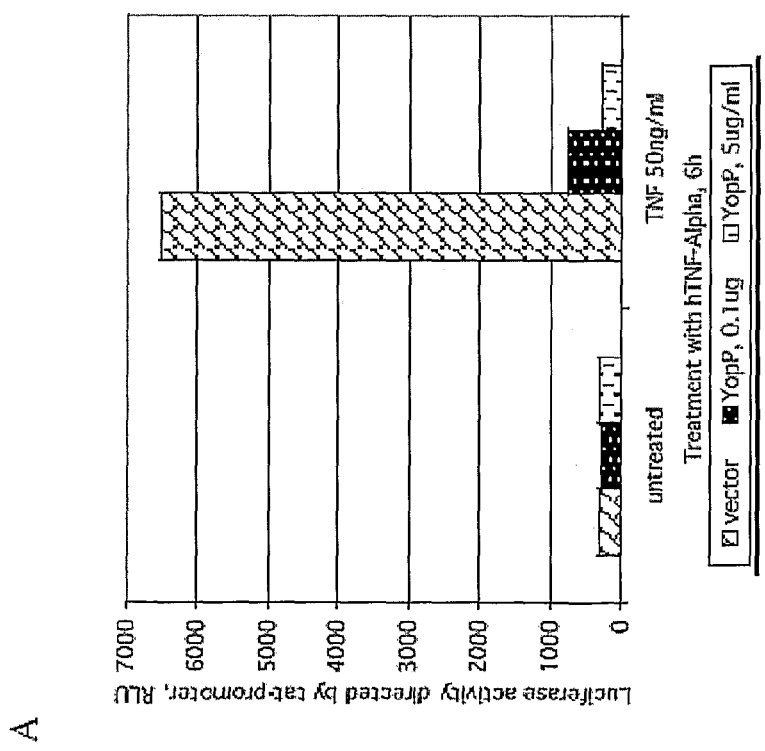

FIGS. 5A-5B show YopP-mediated inhibition of NF-κB activation in 293 cells. FIG. 5A shows YopP inhibition of TNF-mediated NF-κB activation in 293 cells. 293 cells harboring the luciferase reporter gene controlled by the NF-κB inducible tat promoter, were treated with TNF in order to induce NF-κB activation. NF-κB activation was effected in the presence of ectopic YopP. FIG. 5B shows YopP inhibition of NIK-mediated NF-κB activation in 293 cells. 293 cells harboring the luciferase reporter gene controlled by the NF-κB inducible tat promoter, were transfected with NIK to induce NF-κB activation in the presence of ectopic YopP. Luciferase expression increased when NF-κB is induced either by treatment of the cells with TNF or by NIK overexpression. In the presence of YopP the induction of NF-κB was inhibited independently of the agent used for activation.

Figure 6:
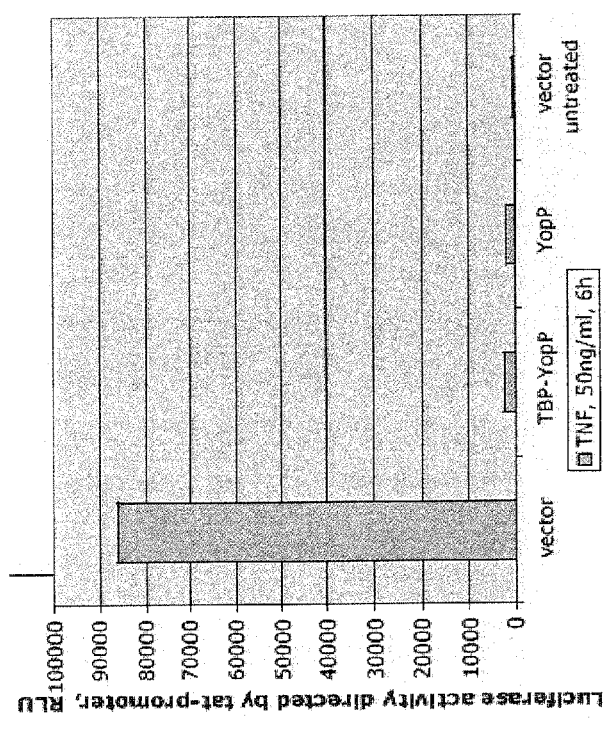
Figure 6:

FIGS. 6A-6B show the expression and activity of TBP-YopP in eukaryotic cells. FIG. 6A shows inhibition of TNF-induced NT-κB activation in eukaryotic cells transiently expressing TBP-YopP. The capability of TBP-YopP to inhibit TNF-mediated NF-κB activation was explored in 293 cells transfected with a reporter vector expressing luciferase controlled by an NF-κB dependent promoter (tat promoter). In addition to the reporter plasmid, the 293 cells were co-transfected with either an expression vector encoding TBP-YopP, YopP or empty vector (pEF6A). The results show that both, the chimeric TBP-YopP and YopP equally inhibited NF-κB and luciferase expression. FIG. 6B shows TBP-YopP expressed in eukaryotic cells. 293 cells were transfected with an expression vector encoding TBP-YopP, YopP or empty vector. Following transfection, the cells were lysed and 25 µl of lysate (or about 100 ng protein) was loaded in each lane of an SDS-PAGE. Lanes 2, 3 and 4, 5 and 6, 7 (from left to right) show duplicate samples of cells transfected with the vector alone (pEF6A-vector), with vector encoding TBP-YopP and vector encoding YopP, respectively. The proteins resolved in the SDS-PAGE were subjected to Western blot analysis and the detection of the recombinant proteins was carried out with antibodies specific to v5 and human TBP-1. FIG. 6B shows that TBP-YopP and YopP migrate with apparent molecular weights of approximately 63 kDa and 37.2 kDa, respectively.

FIGS. 7A-7C show TBP-YopP expressed in bacterial E. coli cells. E. coli cells were transformed with pET-5 expression vector encoding TBP-YopP or pET-5 vector encoding another chimeric protein comprising TBP-1 and a fragment of the Pseudomonas exotoxin including the catalytic domain and translocating domain (TBP-PE38, disclosed in Provisional U.S. application 60/582,827 filed Jun. 28, 2004). Following transformation and isopropyl β-D-thio-galactopyranoside (IPTG) induction, E. coli harboring the pTBP-YopP was lysed and the lysate was fractionated into soluble proteins and insoluble inclusion bodies (IB). Samples of inclusion bodies, dissolved in 8M urea, or total (non-fractionated) lysate were loaded on SDS-PAGE at a concentration of 30 µg per lane and resolved. The proteins in the gels were stained with coomassie blue. Different batches of TBP-Yop are shown on FIGS. 7A and B. FIG. 7C shows the same lysates of FIG. 7B, but subjected to Western blot (1 µg protein was loaded per line) and analyzed using polyclonal rabbit anti-TBP-1 for detection of the chimeric protein. The figure shows that chimeric TBP-YopP is found in inclusion bodies and migrates on SDS-PAGE with an apparent molecular weight of approximately 63 kDa. The arrows indicate the position corresponding to TBP-YopP. Total—total E. coli lysate; IB—inclusion bodies, MW—Molecular Weight standards.

Figure 8:
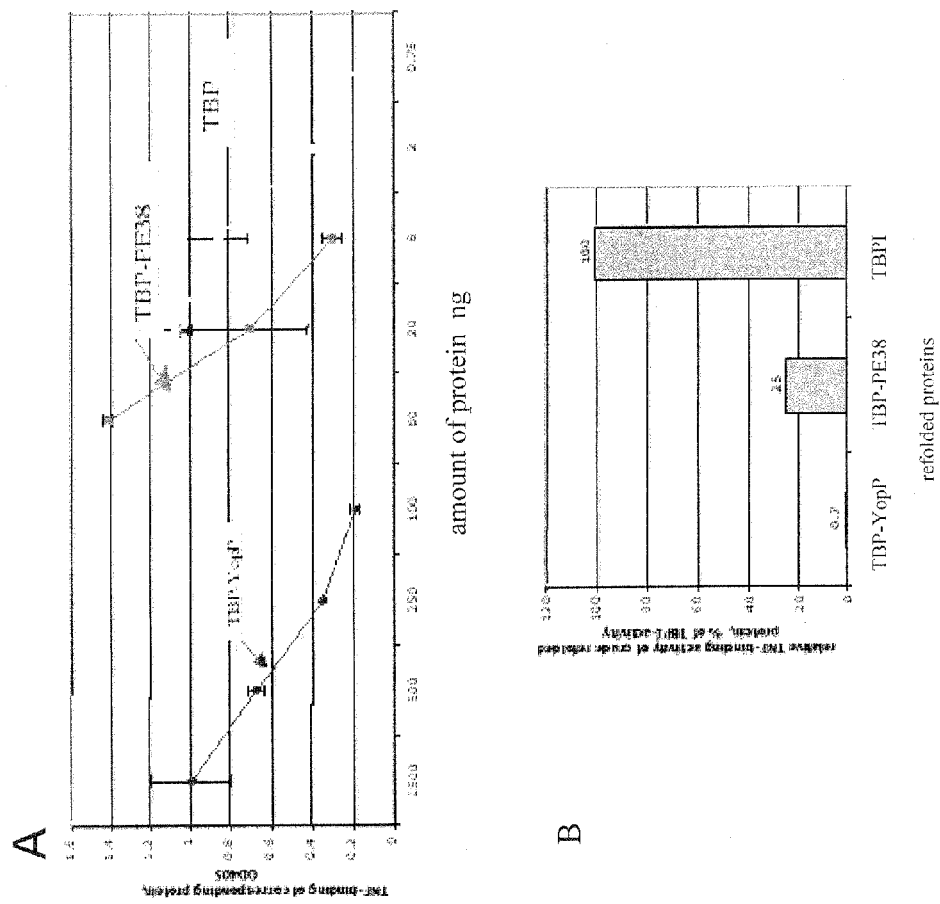

FIGS. 8A-8B show the TNF binding activity of TBP-YopP produced in bacterial cell. FIG. 8A shows TNF binding activity of crude refolded TBP-YopP and TBP-PE38 compared to that of a non chimeric HPLC-purified TBP-1. Binding of TBP-YopP, TBP-PE38 or TBP-1 proteins to TNF was assessed using TNF coated plates. The indicated amount of refolded chimeric proteins or TBP-1 was loaded in TNF coated plates, and binding to the plates was detected by anti TBP-1 antibody. It is shown that, for example, 500 ng of crude refolded TBP-YopP is nearly as active as 20 ng of TBP-PE38 or 5 ng of TBP-1. FIG. 8B shows the % of crude refolded chimeric protein having TNF binding activity. For example, using the activity of TBP-1 as 100% TNF binding, it was found that 0.7% and 25% of refolded TBP-YopP and TBP-PE38 respectively, had TNF binding activity.

Figure 9A:
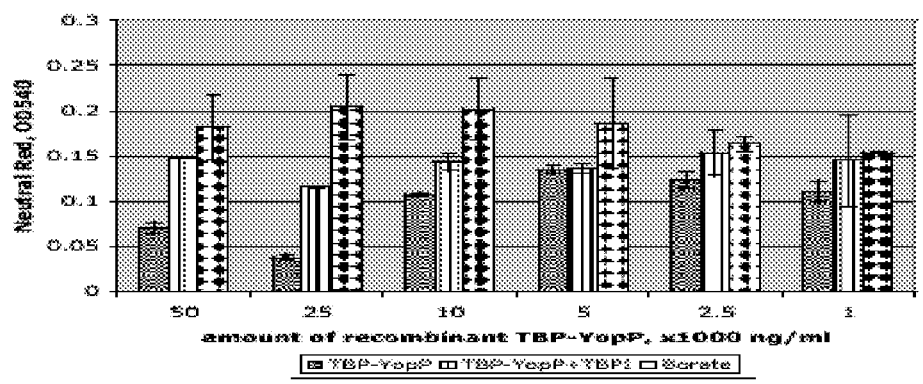
Figure 9B:
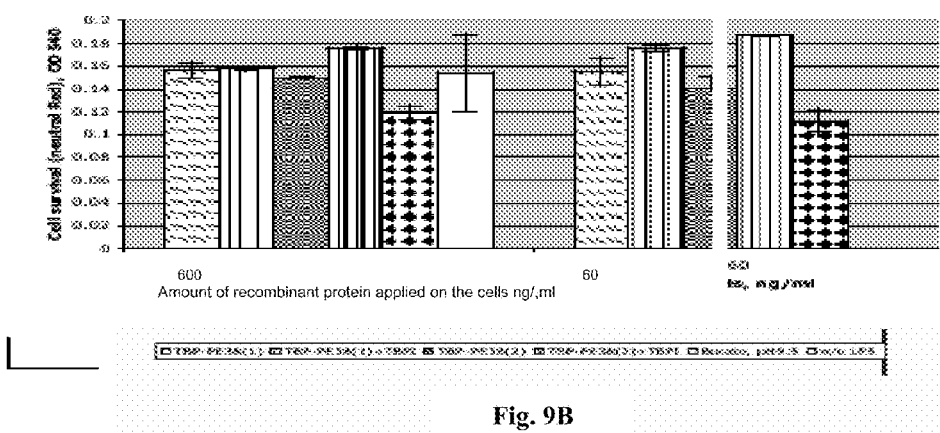

FIGS. 9A-9B show cytotoxicity of TBP-chimeric proteins in activated monocytic like cells. The cytotoxic effect of refolded TBP-YopP (FIG. 9A) and TBP-PE38 (FIG. 9B) assessed on an activated cell line having characteristics of monocytic-like cells (THPI) was evaluated in the presence or in the absence of competing TBP-1. The particular concentrations of TBP-YopP and TBP-PE38 tested, take into consideration that TBP-PE38 exhibits about 36 fold more TNF binding activity than TBP-YopP (see FIG. 8B). It was found that only TBP-YopP had cytotoxic effect on the activated THPI cells and that such cytotoxic effect was specific since it was inhibited by competition with TBP-1. The competitor TBP-1 was applied in 100-fold excess immediately before the chimeric protein. TBP-PE38 (1) and (2) are two different batches of refolded TBP-PE38).

FIGS. 10A-10B show cytotoxicicity of TBP-chimeric proteins in epithelial cells. The cytotoxic effect of TBP-YopP (FIG. 10A) or TBP-PE38 (FIG. 10B) was assessed in a model of epithelial HeLaM9 cells, a cell line engineered to overexpress surface TNF (Pocsik et al., 1995), in the presence or in the absence of competing TBP-1. The particular concentrations of TBP-YopP and TBP-PE38 tested, take into consideration that TBP-PE38 exhibits about 36 fold more TNF binding activity than TBP-YopP (see FIG. 8B). It was found that only TBP-PE38 has cytotoxic effect on the epithelial cell line and that such cytotoxic effect was specific since it was inhibited by competition with TBP-1. TBP-PE38 (1) and (2) are two different batches of refolded TBP-PE38.

Figure 11:
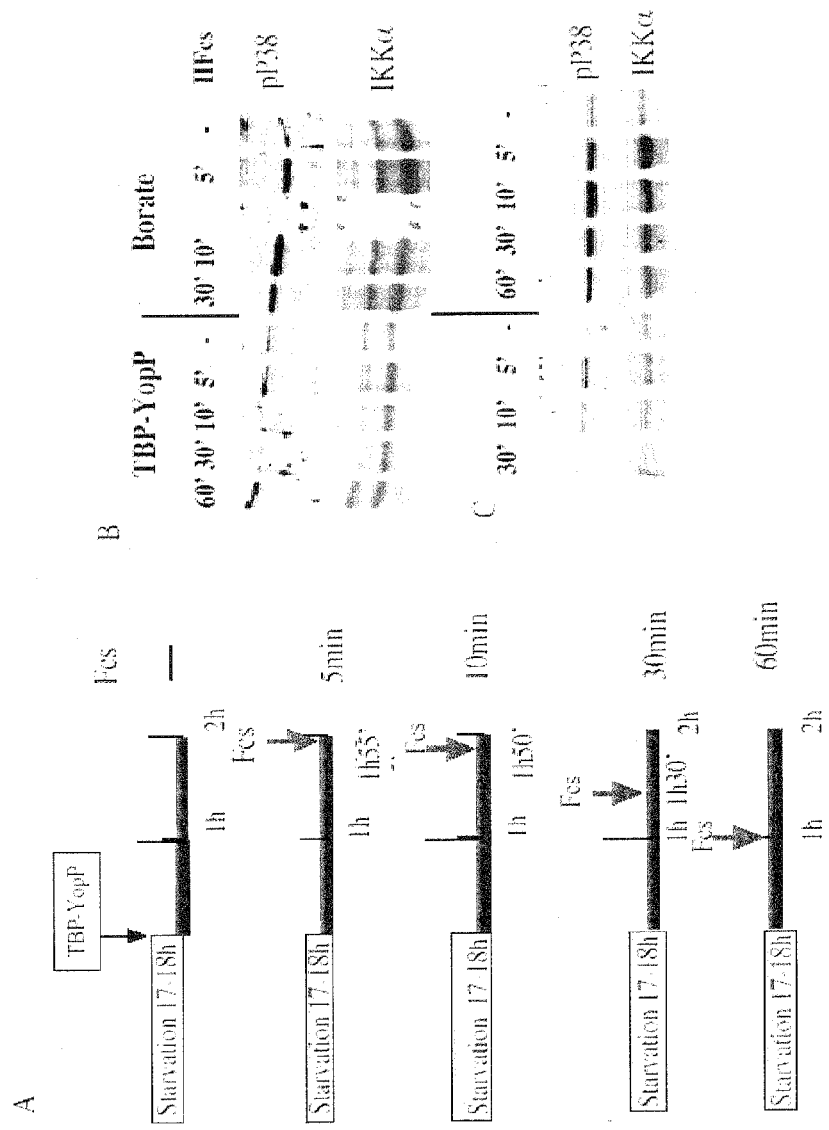

FIGS. 11A-11C show TBP-YopP-mediated inhibition of p38 phosphorylation induced by activation of starved HeLaM9 cells with 10% heat inactivated fetal calf serum (HFcs). FIG. 11A illustrates a schematic representation of the experiment. HeLa M9 cells were starved for 17-18 hours. Then, refolded TBP-YopP was added at concentration of 10 µg/ml for 2 hours and the cells were lysed. 10% HFcs was added at different time points: 5, 10, 30 and 60 minutes prior to cell lysis, as indicated by the arrows on the scheme. Subsequent to activation in the presence or in the absence of TBP-YopP, the cells were lysed, and the cell lysates were subjected to Western blot analysis using pP38 specific polyclonal antibody for detection of phosphorylated p38 (pP38). For normalizing loaded protein in the gel, the same blots were detected with anti IKK-α. FIGS. 11B and C show the results of two experiments where cells were treated as indicated in FIG. 11A or in which TBP-YopP was replaced by the solvent (borate buffer). It was shown that P38 phosphorylation increases upon serum addition and that such serum mediated pP38 phosphorylation is reduced in the presence of TBP-YopP.-untreated starved cells, and 5', 10', 30', and 60' activation of cells for 5 min, 10 min, 30 min and 60 min with 10% HFcs, respectively.

FIGS. 12A-12B shows the effect of the TBP chimeric protein on activated primary macrophage cells. The cytotoxic effect of the indicated concentrations of TBP-YopP (FIG. 12A) or TBP-PE38 (FIG. 12B) was assessed in activated primary macrophage cells, in the presence or the absence of competing TBP-1. Recombinant human TBP-1 was added in 100-fold excess immediately before the chimeric protein. The primary macrophages were activated by treatment with *E. coli* LPS 0111-B4 at indicated concentrations. The particular concentrations of TBP-YopP and TBP-PE38 tested, take into consideration that TBP-PE38 exhibits about 36 fold more TNF binding activity than TBP-YopP (see FIG. 8B). It was found that none of the chimeric proteins had cytotoxic effect on activated primary macrophages.

FIGS. 13A-13B show the effect of TBP-YopP and TBP-PE38 on TNF secretion by activated primary macrophages. The experiment was carried out as described on Example 5. The TNF secreted into the culture medium of LPS-activated primary macrophages in the presence or in the absence of the chimeric proteins was monitored in a bioassay using the TNF sensitive cell line L929 (murine connective tissue clone L929. ATCC Number CCL-1). The culture medium was collected, diluted two, four and eight folds with fresh medium, applied to 1.929 cells, and TNF dependent death of the cells was monitored. It was found that TNF secretion by activated macrophages was inhibited by TBP-YopP but not by TBP-PE38 (FIG. 13B).

DETAILED DESCRIPTION OF THE INVENTION

The present invention relates to a chimeric protein comprising the amino acid sequence of a cell-specific targeting agent and the amino acid sequence of a *Yersinia* outer protein (Yop) connected by a polypeptide enabling translocation of the chimeric protein, or a fragment thereof, from the endosome to the cytosol of the target cell.

According to the invention, a cell specific targeting agent can be any agent capable of binding to a specific cell-surface constituent present in a particular cell. For example, possible targeting agents are an antibody binding a specific cell-surface constituent, a hormone, a cytokine, and preferably the extracellular portion of a receptor for a ligand expressed on the surface of the target cell such as the receptor of the TNF/NGF family. Natural occurrence of soluble forms of receptors have been described for almost all members of the TNF/NGF family, including the two receptors of TNF, CD27, CD30, Fas and others. In one embodiment of the invention, the chimeric protein comprises either a naturally occurring or artificial soluble forms of a receptor of the TNF/NGF family. The whole extracellular domain of any particular receptor of the TNF/NGF family or fragments, muteins, fusion proteins or other functional derivatives thereof can be used. In one embodiment of the invention the chimeric protein comprises the extracellular portion of the TNF receptors; TNF binding protein 1 (TBP-1). In another embodiment of the invention the chimeric protein comprises TBP-2.

The chimeric protein according to the present invention comprises a *Yersinia* outer protein such as YopE. YopM, preferably, YopP and more preferably, a YopP which has reduced or non apoptotic activity such as YopP serogroups O:3, O:9 and O:8 mutated in Arginine-143 which were shown to exhibit less apoptotic activity than YopP serogroup O:8 (Ruckdeschel et al., 2001).

In accordance to the present invention, the polypeptide enabling translocation includes any polypeptide capable of enabling access of a protein into the cytosol. Such polypeptides enabling translocation may derive from bacterial toxins for example, botulinum toxin, anthrax toxin, diphtheria toxin, ricin toxin and preferably pseudomonas exotoxin. In one embodiment of the invention, the polypeptide of *Pseudomonas aeruginosa* exotoxin (see DNA sequence in FIG. 2, SEQ ID NO: 2 and amino acid sequence in FIG. 3, SEQ ID NO: 3) which is deficient in the last a-helix domain (PEtIIr) is used to enable translocation.

The chimeric protein of the invention may include one or more furine cleavage site. In one embodiment of the present invention, two different furine cleavage sites are present in the chimeric protein, namely, one located at the N-terminus of the translocating polypeptide and another located at the N-terminus of Yop and are from *Pseudomonas aeruginosa* exotoxin and Diphtheria toxin origin.

In one embodiment of the invention, a chimeric protein consisting of TBP-1, the translocation domain fragment of *Pseudomonas aeruginosa* exotoxin PEIItr, the furine cleavage site DT and YopP is developed (named TBP-YopP).

The present invention provides TBP-YopP, or a mutein, variant, fusion protein, functional derivative, fragment or salt thereof which are capable of binding TNF and inhibiting NF-κB activity and/or inhibiting TNF release in a cell.

The chimeric protein in accordance with the present invention, was found to bind, penetrate and act in lymphoid cells e.g. macrophage and monocyte and in epithelial cells. TBP-YopP was found to bind and induce cytotoxicity in an activated cell line having characteristics of monocytic cells (THPI). The cytotoxic activity of TBP-YopP was found to be specifically induced through surface TNF of THPI cells. In contrast, TBP-PE38, another chimeric protein (disclosed in Provisional U.S. application 60/582,827 filed Jun. 28, 2004) consisting of TBP fused to the translocation and catalytic domains of pseudomonas exotoxin (PE38) did not cause cytotoxicity of activated THPI cells. TBP-PE38 was found to be cytotoxic for HeLaM9 cell, an epithelial cell line which was engineered to overexpress surface TNF, while TBP-YopP was not cytotoxic to these cells.

The chimeric protein according to the present invention is capable of act on a particular cell in which a given ligand is expressed in surface of such cell in excess, and is capable of "educating" the cell to express lower or normal levels of such ligand. For example, in one embodiment of the inventions TBP-YopP has a desirable and specific effect on activated primary macrophages; it does not induce cytotoxicity and it inhibits TNF secretion.

As used herein the term "muteins" refers to analogs of a protein, in which one or more of the amino acid residues of the naturally occurring components of the protein are replaced by different amino acid residues, or are deleted, or one or more amino acid residues are added to the original sequence of the protein, without changing considerably the activity of the resulting products as compared with the original protein. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes the protein, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch. E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12°20-° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of TBP-YopP, such as to have substantially similar, or even better, activity to TBP-YopP. For example, one characteristic activity of TBP-YopP is its capability of penetrate a specific cell and to cause cytotoxicity and/or to inhibit TNF release and/or signaling of MAPK. Assays for measuring cytotoxicity, TNF secretion, and p38 phosphorylation are described in the examples below. As long as the mutein is capable to have substantial cytotoxic activity in activated THPI cells and/or to inhibit TNF release in activated primary macrophage cells and/or to inhibit pP38 phosphorylation in HeLaM9 cells, it can be considered to have substantially similar activity to TBP-YopP. Thus, it can be determined whether any given mutein has at least substantially the same activity as the chimeric protein of the present invention by means of routine experimentation as shown for TBP-YopP in the examples below.

In a preferred embodiment, any such mutein has at least 40% identity or homology with the amino acid sequence of TBP-YopP. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "percent identity" may be determined. In general, the two sequences to be compared are aligned to give a maximum correlation between the sequences. This may include inserting "gaps" in either one or both sequences, to enhance the degree of alignment. A percent identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984, Nucleic Acids Res. 1984 Jan. 11; 12(1 Pt 1):387-95.), for example the programs BESTFIT and GAP, may be used to determine the % identity between two polynucleotides and the % identity and the % homology between two polypeptide sequences. BESTFIT uses the "local homology" algorithm of Smith and Waterman (J Theor Biol. 1981 Jul. 21; 91(2):379-80 and J Mol Biol. 1981 Mar. 25; 147(1):195-7. 1981) and finds the best single region of similarity between two sequences. Other programs for determining identity and/or similarity between sequences are also known in the art, for instance the BLAST family of programs (Altschul S F et al., 1990 J Mol Biol. 1990 Oct. 5; 215(3):403-10, Proc Natl Acad Sci USA. 1990 July; 87(14):5509-13, Altschul S F et al., Nucleic Acids Res. 1997 Sep. 1; 25(17):3389-402, accessible through the home page of the NCBI at www.ncbi.nlm.nih.gov) and FASTA (Pearson W R. Methods Enzymol. 1990; 183:63-98. Pearson J Mol Biol. 1998 Feb. 13; 276(1):71-84).

Muteins TBP-YopP, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of TBP-YopP may include synonymous amino acids within a group which have sufficiently similar physicochemical properties that substitution between members of the group will preserve the biological function of the molecule (Grantham Science. 1974 Sep. 6; 185(4154):862-4). It is clear that insertions and deletions of amino acids may also be made in the above-defined sequences without altering their function, particularly if the insertions or deletions only involve a few amino acids, e.g. under thirty, and preferably under ten, and do not remove or displace amino acids which are critical to a functional conformation, e.g., cysteine residues. Proteins and muteins produced by such deletions and/or insertions come within the purview of the present invention.

Examples of production of amino acid substitutions in proteins which can be used for obtaining muteins of TBP-YopP, for use in the present invention include any known method steps, such as presented in U.S. Pat. Nos. 4,959,314, 4,588,585 and 4,737,462, to Mark et al; U.S. Pat. No. 5,116, 943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

"Functional derivatives" as used herein cover derivatives of TBP-YopP, and their muteins, which may be prepared from the functional groups which occur as side chains on the residues or are additions to the N- or C-terminal groups, by means known in the art, and are included in the invention as long as they remain pharmaceutically acceptable, i.e. they do not destroy the activity of the protein which is substantially similar to the activity of TBP-YopP.

These derivatives may, for example, include polyethylene glycol side-chains, which may mask antigenic sites and extend the residence of TBP-YopP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carboxylic aroyl groups) or O-acyl derivatives of free hydroxyl groups (for example that of seryl or threonyl residues) formed with acyl moieties.

An "active fraction" according to the present invention may e.g. be a fragment of TBP-YopP. The term fragment refers to any subset of the molecule, that is, a shorter peptide that retains the desired biological activity of TBP-YopP. Fragments may readily be prepared by removing amino acids from either end of TNP-YopP and testing the resultant fragment for its cytolytic properties in activated THPI cells and/or inhibitory effect of TNF release in activated primary macrophage cells and/or inhibition of pP38 phosphorylation in HeLaM9 cells. Proteases for removing one amino acid at a time from either the N-terminal or the C-terminal of a polypeptide are known, and so determining fragments, which retain the desired biological activity, involves only routine experimentation.

As active fractions of TBP-YopP, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to TBP-YopP.

The term "salts" herein refers to both salts of carboxyl groups and to acid addition salts of amino groups of TBP-YopP. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of TBP-YopP.

"Functional derivatives" also comprise multimers made up of TBP-YopP in which changes have been introduced in the sequence of the amino acids making up the TBP-YopP by any conventional method. These changes may comprise elongation or truncation of TBP-YopP molecule or deletion or replacement of one or more amino acids of the TBP-YopP. It is understood that none of the above changes may affect the properties of the chimeric protein.

The procedure for attaching the cell specific targeting agent to the polypeptide enabling translocation and to the Yop may vary. In one embodiment, the cell specific targeting agent is fused to the polypeptide enabling translocation and to the Yop by recombinant means. The genes encoding the two proteins and polypeptide can be isolated as cDNA or in genomic form by any cloning procedure known to those skilled in the art. The proteins and polypeptide may also be linked chemically. This chemical linkage can be carried out by using bifunctional linker molecules such as those available from Pierce Chemical Company, Rockford Ill. (for example BS3 (Bis[sulfosuccinimidyl] suberate).

The fusion between the cell specific targeting agent the polypeptide enabling translocation and the Yop by recombinant means, may be direct, or trough a linking molecule and/or spacer which can be any kind of linker e.g. an amino acid, a peptide or polypeptide, a sulphidril group, a polymer etc. The linking molecule can be a molecule that may be broken upon localization or internalisation of the chimera.

Generating the chimeric protein of the present invention using recombinant DNA methodology, generally involves creating a DNA sequence that encodes the chimeric protein, placing the DNA in an expression cassette, usually present in an expression vector, under the control of a particular promoter, expressing the protein in a host, isolating the expressed protein and, if required, renaturing the protein.

The present invention provides a DNA sequence encoding the chimeric protein of the invention and an expression vector comprising said DNA. The DNA in accordance with the invention, may further encode a signal peptide for the secretion of the chimeric protein produced in eukaryotic cells. A preferred expression vector for production in eukaryotic cells, comprises the DNA encoding the chimeric protein of the invention functionally linked to a promoter having an activity which is independent of NF-kB, for example the EF-1$\alpha$ promoter.

In addition, the present invention relates to a host cell comprising an expression vector comprising a DNA encoding the chimeric protein of the invention. Example of host cells are eukaryotic cells such as HeLa, CHO, 293T, Yeast, insect cells and prokaryotic cells such as $E.\ coli$. Preferably, the host cell is resistant to the cytocidal effect of Yop, such as HeLa M9 (see Example below).

In accordance with the present invention, it is provided a method for producing a chimeric protein in accordance with the invention, comprising culturing the host of the invention, and isolating the chimeric protein produced.

Once expressed, the recombinant chimeric protein of the invention can be purified according to standard procedures of the art, for example purification may include the steps of ammonium sulfate precipitation, affinity columns, column chromatography, gel electrophoresis and the like.

After expression and purifications the chimera may possess a conformation substantially different than the native conformations of the constituent polypeptides. In this case, it may be necessary to denature and reduce the polypeptide and then to cause the polypeptide to re-fold into the preferred conformation.

Denaturation is achieved by exposing the crude material containing the recombinant protein to a combination of chaotropic agents (e.g. urea<or guanidine HCl), reducing agent and high pH. These conditions usually cause solubilization and denaturation of proteins in inclusion bodies. Consequently, a clear solution of proteins is obtained. The proteins, at this stage, are completely opened with no secondary or tertiary structures. The next step is to moderate the extreme conditions of pH, reducing agent and chaotropic agent concentration to enable the folding of the protein. The ability of a protein to fold to its native tertiary structure is dictated by its primary structure. Therefore, lowering the chaotropic and reducing agents concentration and reducing the pH is usually sufficient. However, sometimes fine-tuning of the conditions is required.

The present invention relates to a pharmaceutical composition comprising a chimeric protein of the invention. In one embodiment of the invention, the chimeric protein is TBP-YopP or a mutein, variant, fusion protein, functional derivative, fragment or salt thereof.

The pharmaceutical compositions of this invention are particularly useful for parenteral administration, i.e., subcutaneously, intramuscularly or intravenously. The compositions for parenteral administration will commonly comprise a solution of the antibody or a cocktail thereof dissolved in an acceptable carrier, preferably an aqueous carrier. A variety of aqueous carriers can be used, e.g. water, buffered water, 0.4% saline etc.

Single or multiple administrations of the compositions may be administered depending on the dosage and frequency as required and tolerated by the patient. The concentration of chimeric molecule in these formulations will be so designed as to deliver in the body an amount of molecules sufficient for obtaining a therapeutic effect. In the case of autoimmune diseases, the composition will be designed such as to deliver an amount of chimera that is sufficient to affect the course and severity of the autoimmune disease and to improve the patient's condition, leading to reduction or remission of the disease. The effective amount will depend on the route of administration, the disease to be treated and the condition of the patient.

Among various uses of the chimeric protein of the present invention include treatment or prevention of disease or conditions caused by particular human cells. For example, particular cells in which a given ligand is expressed in excess. The chimeric protein can be administered to kill or to "educate" the cell to express lower or normal levels of the ligand.

In one embodiment, the invention provides the use of the chimeric protein of the invention, preferably TBP-YopP, or a mutein, variant, fusion protein, functional derivative or fragment thereof, in the manufacture of a medicament for treatment of a disease, wherein activity of a ligand of the TNF/NGF receptor is involved in the pathogenesis or the course of the disease.

In a further embodiment, the chimeric protein is used for the treatment of a disease in which TNF plays a pathogenic role such as acute diseases, such as septic shock, graft-versus-host disease (GVHD), malaria, infectious hepatitis, tuberculosis, as well as chronic diseases, such as cancer-associated cachexia, chronic GVHD, rheumatoid arthritis, juvenile diabetes, the inflammatory bowel diseases and psoriasis. Another preferred application is for the treatment of cancer, caused by malignant cells expressing the ligand to which the chimeric protein binds. The chimeric proteins may also be used in vitro, for example in the elimination of harmful cells from bone marrow before transplant.

In another further embodiment, the chimeric protein is used for the treatment of a disease in which activated lymphoid cells such as macrophages or monocytes are involved in the pathogenesis or in the course of the disease for example, septic shock, rheumatoid arthritis, ankylosing spondylitis, psoriasis, amyotrophic lateral sclerosis, Insulin-dependent diabetes mellitus, graft-versus-host disease, and sickle cell anemia.

In yet another embodiment, the chimeric protein is used for the treatment of a disease in which NF-KB activation is involved in the pathogenesis or in the course of the disease, and preferably in which the NF-κB is induced via the canonical pathway.

Having now described the invention, it will be more readily understood by reference to the following examples that are provided by way of illustration and are not intended to be limiting of the present invention.

EXAMPLES

Example 1

Construction of a Chimeric Gene Comprising the Extracellular Portion of the p55 TNF Receptor (TBP-1) the Truncated Translocation Domain of *Pseudomonas* Exotoxin II (PEIItr) the *Diphtheria* Toxin Furine Cleavage Site (DT) and the *Yersinia* YopP Protein (Referred Herein as TBP-YopP)

Figure 1B:
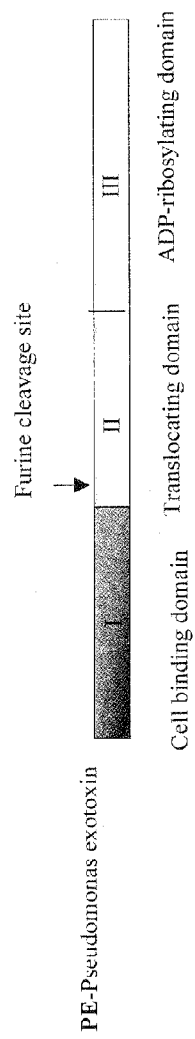

In order to prepare the chimeric TBP-YopP gene (SEQ ID NO: 1, FIG. 1C), as schematically represented on FIG. 1A, each of the DNA fragments encoding the soluble form of the p55 TNF receptor, the truncated translocation domain of *Pseudomonas* exotoxin II lacking the last (F) α-helix (FIG. 2, SEQ ID NO: 2 and FIG. 3, SEQ ID NO: 3 DNA and amino acid sequences, respectively), and the *Diphtheria* toxin furin cleavage site fused to the toxin YopP were prepared and amplified by Polymerase Chain Reaction (PCR) and ligated.

The amino acid sequence of the soluble form of the p55 TNF receptor (TNFRSF1A, Genbank ID M75866) corresponds to that of the major species of the soluble form of this receptor (TBP-1) that had been isolated from human urine (U.S. Pat. No. 5,811,261) and it extends from Asp 41 to Asn 201 in the receptor's extracellular domain (Swiss-Prot accession number: P19438). The soluble form of the p55 TNF receptor, TBP-1, was isolated by PCR (1) amplification (with High fidelity Taq polymerase from Boehringer Mannheim) using full length TNFRI (plasmid pc55) as the template (plasmid pc55 described in Nophar et al., 1990) and the following primers:

```
Forward primer:
CATCATATGgatagtgtgtgtccccaagg     (SEQ ID NO: 4)
```

This primer has the Nde I restriction site (needed later for inserting the chimeric gene into the expression vector) followed by 20 nucleotides overlapping the 5' end of TBP-1 (the coding sequence is italicized).

```
Reverse primer:
AGGAAGCTTTattctcaatctggggtaggcac     (SEQ ID NO: 5)
```

This primer has 22 nucleotides overlapping the complementary 3' end of TBP-1 followed by nucleotides encoding the Hind III restriction site (needed later for ligating the TBP DNA to the DNA encoding PEIItr).

The DNA sequence (SEQ ID NO: 2) encoding a polypeptide sequence corresponding to residues 278 to 384 (SEQ ID NO: 3) of *Pseudomonas aeruginosa* exotoxin typeA gene (accession number K01397, NCBI Gene Bank), PEIItr, was isolated by PCR amplification using genomic DNA of serotype 61 of *Pseudomonas aeruginosa* (Leitner G. Kimron Veterinary Institute, Israel) as the template, and the following primers:

```
Forward primer:
                                      (SEQ ID NO: 6)
AATTAAAGCTTccggaggtcccgagggcggcagcctggccgcgctgaccg
cg
```

This primer has nucleotides encoding the Hind III restriction site (needed for the ligation of PEIItr to the above amplified TBP-1 DNA), followed by 14 nucleotides encoding a linker sequence, ccggaggtcccgag, and followed by 27 nucleotides overlapping the 5' end of the PE domain II corresponding to nucleotides 1577-1603 of exotoxin A (accession number K01397).

```
Reverse primer:
                                           (SEQ ID NO: 7)
    GTGAATTCTTACCCGGGgtcgttgccggtgccctgccg.
```

This primer has the SmaI restriction site and nucleotides 1894-1874 complementary to DNA encoding residues of PE prior to 384 and including 384 amino acid residue. It comprises the complementary nucleotides encoding the amino acid residues prior to and including amino acid 384 of PE (gtcgttgccggtgccctgccg), a stop codon and the SmaI (cccggg) and EcoRI (gaattc) restriction sites (needed later for the ligation to the DT-YopP DNA fragment isolated below). The PEIItr fragment (the PCR2 product) was inserted into the HindIII/EcoRI sites of pET-vector prior to ligation to DT-YopP (PCR3 product see below).

A third (PCR 3) was carried out in order to prepare the DNA encoding the YopP ligated at its 5' end with DNA encoding *Diphtheria* toxin (DT)-furin cleavage site (RVRR). For PCR 3, DNA encoding the YopP effector of *Yersinia entherocolitica* serotype 0:8, residues 1-864 were used as the template (TrEMBL, accession number Q93KQ5) and the following primers:

```
Forward primer:
                                          (SEQ ID NO: 8)
ATCCCGGGagagtgagaagaatgattgggccaatatcacaaataaacagc
```

This primer comprises the nucleotide sequence of SmaI (needed later for the ligation to TBP-1-PEIItr), followed by 12 nucleotide encoding the DT furin cleavage site (RVRR) and 31 nucleotides overlapping the 5' end of YopP gene.

```
Reverse primer:
                                          (SEQ ID NO: 9)
CAGAATTCttatactttgagaagtgttttatattcagc
```

This primer comprises 30 complementary nucleotides overlapping the 3' end of YopP gene and the restriction site of EcoRI (needed later for the ligation to TBP-1-PEIItr).

In order to obtain the PEIItr-DT-YopP fragment, the above amplified DT-YopP (PCR 3 product) DNA fragment was subjected to digestion with SmaI and EcoRI followed by ligation to PEIItr through the compatible ends.

To obtain chimeric TBP-PEIItr-DT-YopP fragment flanked by NdeI/EcoRI sites, TBP-1 (PCR 1 product) was inserted into NdeI/HindIII site of a pET based-vector containing PETIItr-DT-YopP. The vector encoding the chimeric TBP-PEIItr-DT-YopP gene, pTBP-YopP, was transformed and amplified in an *E. coli* strain (DH5α), and purified by methods known in the art.

Example 2

Assessment of NF-κB Inhibiting Activity of TBP-YopP in Eukaryotic Cells

YopP inhibits NF-κB, a transcription factor known to be central in the onset of inflammation. The following experiments were carried out to test, prior to production of the protein in bacterial inclusion bodies and refolding of solubilized protein, whether chimeric TBP-YopP protein retains the NF-κB inhibitory activity in eukaryotic cells.

Initially, in order to search for an appropriate promoter for expression of YopP in eukaryotic cells, experiments were carried out with a vector comprising YopP alone. For this purpose YopP DNA was inserted into two different eukaryotic vectors, pcDNA3-HisA and pEF6-v5-HisA (Invitrogen). pcDNA3-HisA and pEF6-v5-HisA have different promoters, CMV and EF-1α, respectively. These vectors allow production of tagged proteins. To obtain tagged YopP protein, the stop codon of YopP was mutated by PCR to encode Valine. Tagging YopP allows detection of expressed YopP in Western blot analysis by using tag specific antibodies.

YopP and GFP were expressed in 293 cells by co-transfecting pcDNA3 based vectors encoding His-T7-YopP and the reporter gene His-T7-GFP, both, under the control of the CMV promoter. In parallel, YopP-v5 and the reporter gene β-galactosidase-v5 were expressed in 293 cells by co-transfecting pEF6 based vectors encoding YopP-v5 and the reporter gene β-galactosidase-v5, both, under the control of the EF1-α promoter.

As shown in FIG. 4B, expression of His-T7-YopP controlled by a CMV promoter was too weak to be visible by Western blot analysis using anti-T7 antibody for detection. The CMV promoter contains three strong NF-κB binding sites (FIG. 4C). Thus, presumably, expression of a protein controlled by the CMV promoter was inhibited by the potent inhibitor of NF-κB, YopP.

The results observed in FIG. 4B also show that increasing YopP plasmid concentrations in the transfection reactions from 1 to 5 μg, resulted in a decrease of GFP-expression, most probably caused by inhibition of the CMV promoter as well.

In contrast, YopP was readily detected when expressed under the EF-1α promoter (FIG. 4A). Also, YopP did not inhibit expression of the reporter gene, β-galactosidase, expressed under the EF-1α promoter (FIG. 4A).

Because the activity of the EF-1α promoter, unlike the CMV promoter, is independent of NF-κB activity (FIG. 4C), the YopP and the chimeric TBP-YopP was efficiently expressed under the control of the EF-1α promoter.

The following experiment was carried out to check whether YopP expressed under the control of the EF-1α promoter, inhibits NF-κB activation in eukaryotic cells. In order to check the NF-κB inhibitory activity of YopP, 293-cells were co-transfected with a pEF6-v5-HisA encoding YopP or with an empty pEF6-v5-HisA vector and a vector encoding luciferase under the NF-κB inducible tat-promoter and, 48 hours post transfection the cells were either treated with TNF to induce NF-κB activation or remained untreated the cells were lysed and luciferase expression (activity) was measured.

To induce NF-κB activation, 48 hours after transfection, 293 cells were treated with 50 ng/ml recombinant human TNF-α for 6 hours. After induction with TNF-α the cells were washed with PBS three times, lysed on ice in triton/glycylglycyne lysis buffer (1% triton X-100, 25 mM glycylglycine, pH7.8, mM MgSo4, 4 mM EGTA, 1 mM DTT), and the lysates was diluted four times in assay buffer (25 mM glycylglycyne, pH7.8, 15 mM MgSO4, 4 mM EGTA, 1 mM DTT, 15 mM K3PO4, pH7.8 (or Na2HPO4). To measure luciferase activity, 2 mM ATP and 200 μM luciferin were added.

As shown in FIG. 5A, TNF-α treatment (and NF-κB activation) of cells transfected with vector alone (pEF6-v5-HisA) showed an increase of more than 6,000 luciferase units compared to non-treated cells. Inhibition of luciferase expression (and inhibition of NF-κB activation) was observed when, instead of empty vector, a vector encoding YopP (0.1 0r 5 μg) was used.

Alternatively, NF-κB activation can be induced by overexpressing NIK (Swiss-Prot primary accession number Q99558, Name: mitogen-activated protein kinase kinase kinase 14, Synonym: NF-kappa beta-inducing kinase). The NF-κB inhibitory action of YopP was assessed also on NF-κB activation mediated by overexpression of NIK. FIG. 5B shows that transfecting the cells with an expression vector encoding NIK (pNIK) induced NF-κB activation 48 hours after transfection and that co-transfection of pNIK and the vector encoding YopP, prevented NF-κB activation.

The possibility that YopP inhibition of NIK-mediated NF-κB activation is caused via inhibition of the alternative pathway of NF-κB activation was explored. For this purpose, metabolic changes that are specific of NF-κB activation by the alternative pathway were measured following NF-κB activation induced in the presence or in the absence of YopP. For example, changes in degradation of p100 and appearance of p52 were monitored following NIK-mediated NF-κB activation in the presence or in the absence of ectopic added YopP.

Based on the above results, the EF-1α promoter was elected to control expression of the chimeric TBP-YopP in eukaryotic cells. In order to ligate the NdeI-EcoRI flanked TBP-YopP insert into the BamHI/EcoRI cloning site of the pEF6-v5-HisA vector, the NdeI and BamHI protruding sites of the insert and vector, respectively, were filled in prior to ligation. After ligation the resulting plasmid was named TBP-YopP/pEF6.

In order to check NF-κB inhibitory activity of TBP-YopP, 293-cells were co-transfected with either empty vector, TBP-YopP/pEF6 or pYopP-v5-His and with a reporter vector encoding luciferase under the NF-κB inducible tat-promoter. To induce NF-κB activation, 48 hours after transfected, the cells were treated with 50 ng/ml recombinant human TNF-α for 6 hours. After induction with TNF-α the cells were washed with PBS three times, lysed on ice in triton/glycylglycyne lysis buffer (1% triton X-100, 25 mM glycylglycine, pH7.8, 15 mM MgSo4, 4 mM EGTA, 1 mM DTT), and the lysates were diluted four times in assay buffer (25 mM glycylglycyne, pH7.8, 15 mM MgSO4, 4 mM EGTA, 1 mM DTT, 15 mM K3PO4, pH7.8 (or Na2HPO4). To measure luciferase activity, 2 mM ATP and 200 µM luciferin were added.

Lysates of cells transfected with vector alone and treated with TNF-α showed an increase of more than 80,000 luciferase units (namely, NF-κB activation) compared to lysates of non-treated cells. Inhibition of luciferase expression (namely, inhibition of NF-κB activation) was observed when, instead of empty vector, a vector encoding either YopP alone or TBP-YopP chimera was used (FIG. 6A). Western blot analysis of lysates from TBP-YopP/pEF6 transfected cells using anti-v5 and anti-TBP-1 antibody revealed that the full length chimeric TBP-YopP was expressed in the cytoplasm of eukaryotic cells with an apparent molecular weight of about 63 kDa (FIG. 6B). The chimeric protein was not cleaved by furin or furin-like proteases, since by being expressed from a plasmid, the chimeric protein did not enter the Golgi or endosomes, the organelles in which the furin and furin-like proteins act.

The results obtained show that, once in the eukaryotic cell, the chimeric TBP-YopP protein is capable of inhibiting NF-κB activity as efficiently as YopP alone.

Example 3

Production of TBP-YopP in Bacterial Cells

After verifying that TBP-YopP is active in eukaryotic cells (see preceding Example), the chimeric protein was produced in bacterial cells as follows:

Competent BL-21/pLysS (DE3) cells were transformed with the vector containing TBP-YopP (pTBP-YopP, see Example 1) and seeded in 2YT agar plates containing ampicillin and incubated over night (about 16 hours) at 30° C. The cell transformants were collected from the agar plates and suspended in 5 ml 2YT per plate. The collected bacterial cells were cultured in 3 liters of 2YT with 200 µg/ml carbenicillin and incubated at 30° C. until the O.D.$_{600}$ of the cell culture was 0.6. Then, the cells were transferred to 20° C. and treated with 1 mM isopropyl β-D-thio-galactopyranoside (IPTG) for induction of recombinant protein expression. 200 µg/ml rifampicin (stock solution of 100 mg/ml in DMSO) were added to the cells 45 minutes after IPTG addition. The cell culture was allowed to grow at 20° C. for 5 hours collected by centrifugation (6000 rpm, 10 min., 4° C.), and the obtained cell pellet kept frozen at −70° C.

In order to prepare cell lysates, the frozen cell pellet was thawed on ice and re-suspended in 100 ml of buffer A [phosphate buffered saline without calcium and magnesium ("PBS w/o"), 50 mM EDTA, 5 mM MgSO$_4$, lour tablets of complete protease cocktail (Roche), 30 mg/l DNaseI (Sigma)]. To breakdown cell clumps, the bacterial suspension was sonicated on ice. Full bacterial lysis was obtained by the following method: 3×35 ml of cells was French pressed at 5000 psi, and then twice at 15000 psi. Then, lysed cells were centrifuged at 15,000 rpm at 4° C. 50 min (27,000×g) on a Sorval centrifuge, employing SS-34 rotor. The pellet was resuspended in 40 ml of "PBS w/o", containing 20 mM EDTA, and 3% triton X-100 and sonicated on ice to resuspend the inclusion bodies. Inclusion bodies, which were released from the lysed cells, were precipitated by ultracentrifugation at 27,000×g at 4° C. for 50 min. The inclusion bodies were washed with 40 ml PBS containing 20 mM EDTA and triton for two more times, and with 40 ml PBS containing 20 mM EDTA in the absence of triton for three times.

The inclusion bodies, containing most of the recombinant protein (as judged by SDS-PAGE FIG. 7A), were dissolved in denaturation solution comprising 8M urea; containing 5 mM 2-mercaptoethanol titered to pH 12-12.8. The volume of the denaturation solution used was equal to 443 times the inclusion body's wet weight. To promote full dissolution of the inclusion bodies, the solution was vigorously vortexed and sonicated on ice.

The protein was re-natured by 10-fold dilution with 50 mM borate buffer at pH 9.5 and incubation for 18-20 hours at 4° C. with gentle stirring (200 rpm).

2.5 liters of refolded protein was 15-fold concentrated by ultracentrifugation trough ultrafilter PM30 (Amicon), and the final volume of the concentrated protein was about 170 ml. The protein concentration of the refolded crude protein was estimated by Bradford reagent (Sigma) to be about 100 µg/ml. TBP-YopP fusion protein was estimated to be about 10% of the refolded crude protein (as estimated by densitometry of the protein band in SDS-PAGE). Therefore from 3 liters of bacterial culture about 1.7 mg of chimeric TBP-YopP protein were obtained, or from 500 mg inclusion bodies 17 mg of total crude protein was obtained of that near 1% (about 170 ng) was active chimeric TBP-YopP protein (see Example 4 below).

Figure 7:
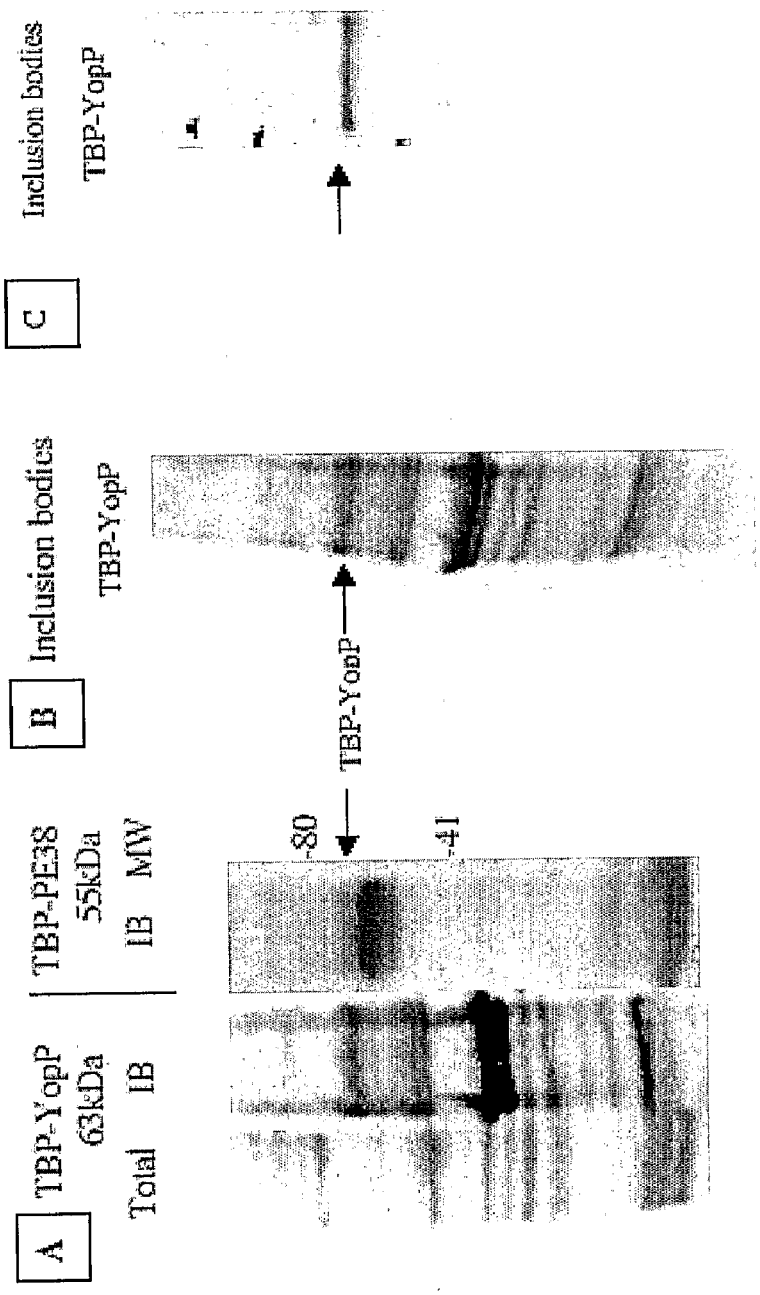

The results obtained show that the chimeric TBP-YopP produced in bacterial inclusion bodies can be refolded and had the correct size of 63 Kda (FIG. 7).

Example 4

Binding of the chimeric TBP-YopP protein to TNF. The following experiment was carried out to assess whether the refolded TBP-YopP, protein produced in bacterial cells (see Example 3), retains the TNF binding activity.

Figure 10:
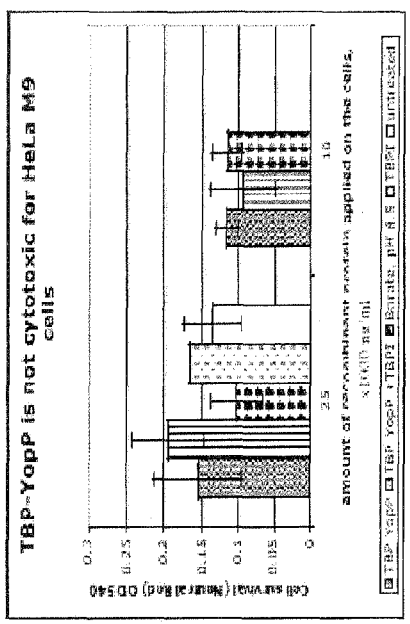
Figure 10:
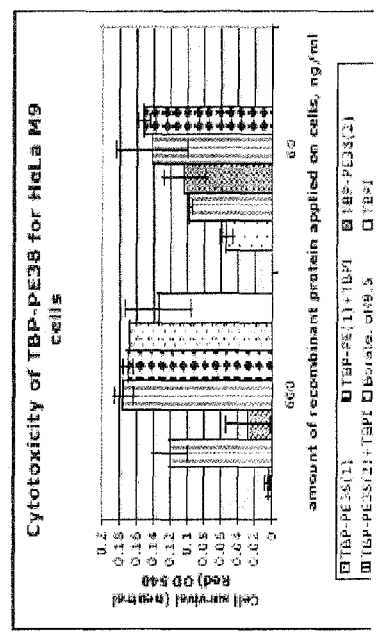

Binding of TBP-YopP to TNF was assessed employing TNF coated plates. The binding of TBP-YopP to TNF was compared to the binding of non chimeric recombinant human TBP-1 (HPLC purified of CHO origin) to TNF, and to the binding of TBP-PE38, another chimeric protein comprising TBP-1 fused to the translocating and catalytic domain of *Pseudomonas aeruginosa* exotoxin, (disclosed in the Provisional U.S. application 60/582,827 filed Jun. 28, 2004) to TNF (FIG. 8).

96-well microtiter plates were coated with TNF by incubating the plates with a solution of 2 mg/ml purified TNF in 0.1 M $Na_2CO_3$, pH 9.6 containing 0.02% $NaN_3$ for 16 h at 4° C. After incubation, the wells were then rinsed with PBS and further incubated for 3 h at 37° C., with 0.2 ml/well PBS containing 3% BSA, 0.02% NaN3 (blocking solution). 50 µl samples of TBP-YopP, TBP-1 or TBP-PE38 were applied per well containing the amount of protein indicated on FIG. 8A (in triplicates) and the plates were incubated for 1 h at 37° C. When necessary, the samples were diluted in blocking solution. Following 1-hour incubation, the plates were washed three times with blocking solution. 50 µl of rabbit anti-TBP-1 antibody, diluted 1:1000 in blocking solution was added to the wells, incubated for one hour at 37° C., or over night at 4° C. and washed three times with blocking solution. 50 µl of secondary antibody anti-rabbit-HRP, diluted 1:1000 was added to the wells, incubated for one hour at 37° C. and washed away three times with blocking solution. 100 µl of fresh prepared solution ABTS, containing 0.01% $H_2O_2$ was added and incubated 30 minutes at 37° C. The presence of the TBP or chimeric TBP was detected by the appearance of a green color whose intensity was measured at 405 nm.

In the TNF-binding assay summarized in FIG. 8, taking TNF-binding activity of HPLC-purified TBP-1 as 100% (FIG. 8B), the binding capacity of crude refolded TBP-YopP to TNF-α was found to be about 0.5-1% (FIG. 8B). Taking in consideration that refolded TBP-YopP is only 5-10% of total protein of inclusion bodies (see preceding Example and FIG. 7), we concluded that at least 10% of the protein is properly refolded. Thus, the efficiency of TBP-YopP refolding was found to be similar to the efficiency of refolding of TBP-PE38, near to 10% (U.S. Provisional Application No. 60/582,827 filed on Jun. 28, 2004). The main difference was, that refolded TBP-PE38 represented more than 30% of the crude protein in inclusion bodies.

The results obtained show that the chimeric TBP-YopP produced in bacteria was correctly refolded and capable of binding TNF.

Example 5

Activity of Refolded TBP-YopP in situ

During infection of *Yersinia* YopP is injected into the cells. Once inside the cells, YopP is known to suppress TNF-α release and to induce apoptosis in infected macrophages (Cornelis G. R Nature 2001). The following experiments were designed to check cytotoxicity of TBP-YopP in comparison to another chimeric protein, TBP-PE38, comprising TBP-1 fused to the translocating and catalytic domain of *Pseudomonas aeruginosa* exotoxin (disclosed in U.S. Provisional Application No. 60/582,827 filed on Jun. 28, 2004) in 3 different cells: LPS activated human monocytic THPI cell lines, human epithelial HeLaM9 cell line overexpressing surface TNF-α and mouse LPS-activated primary macrophages. To test specificity, non-chimeric human recombinant TBP-1 was applied immediately before the chimeric proteins to some wells to compete for TNF binding.

In order to explore cytotoxicity of the chimeric proteins on a macrophage-like cell line, THPI cells (Example 7) were seeded at density 200,000 cells per well in 96-well plate in Fcs-free RPMI, containing insulin, 1 mkg/ml, transferrin, 1 µg/ml, Na selenite, 1 ng/ml, Na pyruvate, non-essential amino acids, glutamine with PM 50-100 ng/ml for 16 h (to induce macrophage like phenotype and exposure of the LPS receptor). Then LPS *E. coli* (0111-B4) was added at a concentration 1 µg/ml (to induce TNF expression) together with GM6001 (a metalloproteinase inhibitor to prevent TNF shading from the cell surface), at a concentration of 10 µg/ml for 1-1.5 hours. The resulting PMA-LPS-GM6001-treated THPI cells show a phenotype characteristic of macrophage cells having a large amount of surface TNF. These macrophage-like cell lines were incubated with various concentrations of refolded TBP-YopP or TBP-PE38 for about 20 hours and stained with neutral red for estimating survival. When indicated, recombinant human TBP-1 was added immediately before the refolded chimeric protein to compete for cell surface TNF. As shown on FIG. 9A, TBP-YopP causes cell death of 50-75% of activated THPI cells at concentrations of 25 and 50 µg/ml. Taking in consideration that active TBP-YopP composes only near 1% of crude refolded protein (FIG. 8B), we estimated that the effective concentrations of TBP-YopP being as low as 0.25 µg/ml. TBP-1 was found to completely protect the cells from toxicity of TBP-YopP when applied in 100-fold excess, indicating that the cytotoxic effect of TBP-YopP is specifically induced trough the surface TNF of activated THPI cells.

In contrast, it was found that the other chimeric protein, TBP-PE38, did not cause cell death of activated THPI cells (FIG. 9B).

The results obtained demonstrate that TBP-YopP specifically binds to surface of activated monocytic-like cell line, penetrates into the cells and causes cell death.

In order to test cell specificity of TBP-YopP cytotoxicity, the cytotoxic effect of TBP-YopP was assessed in HeLaM9, an engineered epithelial cell line overexpressing membrane bound TNF (Example 7).

HeLaM9 cells were seeded at density 100,000 cells per well in 96-well plate in RPMI with 10% Fcs. After adhesion, the indicated concentrations of refolded chimeric protein, TBP-YopP or TBP-PE-38 respectively, were added to the wells and incubated for about 20 hours. When indicated, recombinant human TBP-1 was added immediately before the refolded chimeric protein to compete for binding to TNF on cell surface. Following 20 hours incubation, the cells were stained with neutral red to estimate cell survival.

The results shown on FIG. 10, demonstrate that TBP-YopP was not cytotoxic to epithelial HeLaM9 cells at concentration as high as 25 µg/ml, a concentration that was shown to cause about 75% cell death of THPI cells (FIG. 9A).

In contrast, TBP-PE38 caused more than 90% cell death in HeLaM9 cells at concentrations of 0.6 µg/ml, a concentration of TBP-PE38 that was shown to lack any cytotoxic effect in THPI monocytic cell line (FIG. 9B). TBP-1 prevented the cytotoxic effect of TBP-PE38, indicating specificity of TBP-PE38 action trough TNF binding. One of the batches of TBP-PE38 was very active and was cytotoxic at concentrations as low as 0.06 µg/ml, killing for nearly 65% of HeLaM9 cells.

In all, these data show that, once inside the cells, TBP-YopP is cytotoxic to macrophage like cell lines but not to epithelial HeLa M9 cells. Experimental evidences were obtained (see Example 6 below) indicating that although TBP-YopP is not cytotoxic to HeLa M9 cells it does bind surface TNF and penetrates into HeLaM9 cells, as evidenced by TBP-YopP inhibition of p38 phosphorylation caused by serum activation following starvation (see Example 6 and FIG. 10).

The activity of refolded TBP-YopP was also tested in LPS-activated primary macrophages. For the preparation of primary macrophages, female mice C57BL/6 was injected intraperitoneally (i.p.) with 1.5 ml sterile Brewer's thioglycolate broth (Difco) for 4 days. The peritoneal exudates (>85% macrophages) was harvested at day 4, washed with PBS by centrifugation and seeded in 96-well flat bottom plates at 1×100,000 macrophages/well in RPMI with 10% heat inactivated Fcs. The cells were allowed to adhere for 18 h. Non-adherent cells were removed by washing with warm medium.

Figure 12:
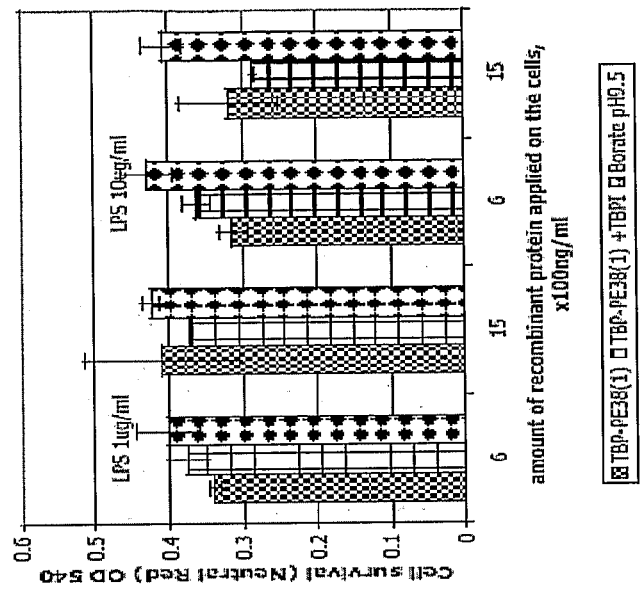
Figure 12:
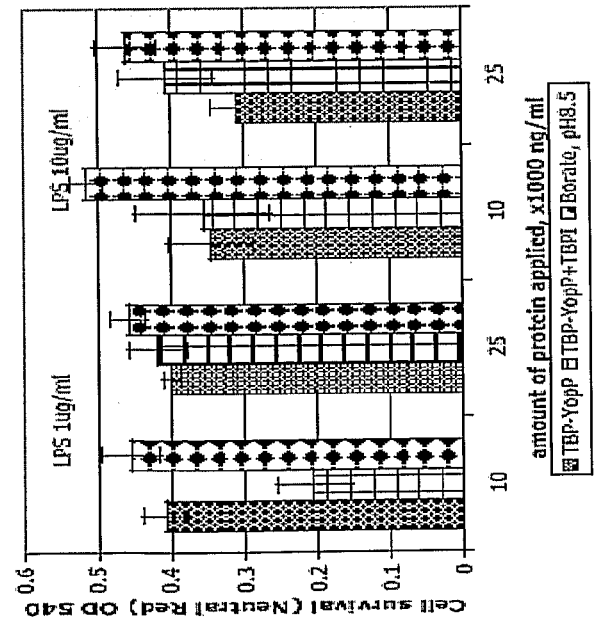

For inducing macrophage activation, a macrophage monolayer was treated with the LPS (*E. coli* LPS 011:B4) at concentrations indicated in FIG. 12 (1 µg and 10 µg) for 1 h in presence of 5 µg/ml GM6001 (Calbiochem). After induction, the cells were incubated for two more hours in the presence or in the absence of refolded TBP-YopP or TBP-PE38. Next, the medium was replaced for RPMI+10% HFcs with the same concentration of LPS, but without GM6001 to allow for secretion of TNF-α into the cell culture medium. The cell culture medium of over night-incubated macrophages was collected and the TNF-α measured by a bioassay. The cell monolayers were stained with neutral red to measure cell survival.

The results obtained, summarized in FIG. 12, show that neither of the chimeric proteins, TBP-YopP or TBP-PE38, was cytotoxic for activated primary macrophages.

Figure 13:
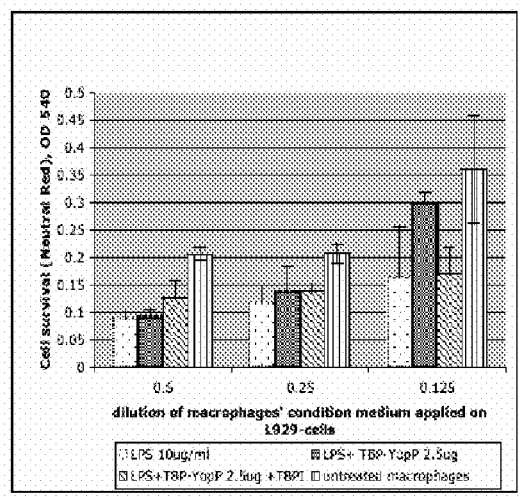
Figure 13:
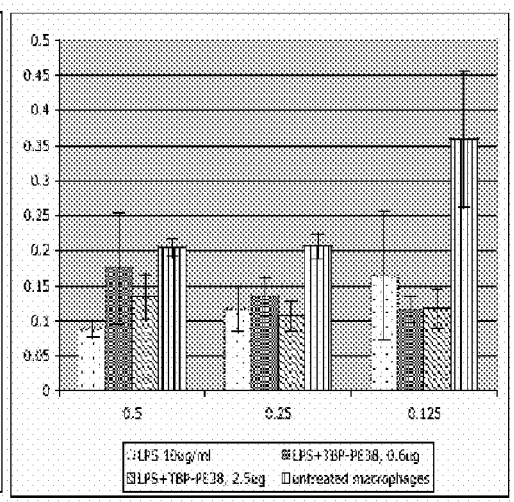

Since YopP is known to inhibit TNF secretion, the levels of TNF secreted in the growth medium of LPS-activated primary macrophages incubated in the presence or in the absence of TBP-YopP was assessed (FIG. 13). Medium of activated primary macrophages was collected, diluted two, four and eight folds (0.5, 0.25, 0.125 respectively) with fresh medium and applied on a monolayer of TNF sensitive cells (L929) seeded at density $1 \times 10^5$ cells per well (on 96-well plates). The bioassay was carried out in presence of 10 µg/ml cycloheximide. L929 cells (murine connective tissue clone L929 ATCC Number CCL-1) were incubated with the conditioned medium of activated macrophages and incubated for 20 hours. The level of L929 cytotoxicity is proportional to the concentration of TNF present in the conditioned medium of activated primary macrophages.

As shown on FIG. 13, thioglycolate-treated peritoneal macrophages produced some TNF-α. For example, two or four fold diluted medium of the thioglycolate treated peritoneal macrophages caused death of more than 40% TNF-sensitive L929 cells. However, additional macrophage activation by LPS augmented TNF secretion. For example, cell death was higher than 60% when exposed to eight fold diluted conditioned medium of activated macrophages (FIG. 13A, B). Conditioned medium of activated primary macrophages in the presence of TBP-PE38 was found to be equally toxic for L929 as conditioned medium of activated macrophages in the absence of TBP-PE38 (FIG. 13B). This result indicates that TBP-PE38 does not inhibit TNF secretion in primary activated macrophages. In contrast, the conditioned medium of macrophages activated in the presence of TBP-YopP was considerably less toxic to L929 cells in comparison to conditioned medium of macrophages activated in the absence of TBP-YopP. For example, when conditioned medium of macrophages activated in presence of TBP-YopP was eight fold diluted (0.125 on FIG. 131A), the amount of TNF was too low to be cytotoxic for L929 cells. Lower dilutions such as four fold or two fold dilutions (FIG. 13A, 0.5, 0.25) still contained enough TNF to kill 60-70% of L929 cells. Incubation of macrophages with TBP-1 in combination with TBP-YopP completely prevented the inhibitory effect of TBP-YopP on TNF production (FIG. 13B 0.125). In this case, cell death was about 60%, i.e. the same level of cell death observed using conditioned medium of activated macrophages in the absence of TBP-YopP.

These results show that neither TBP-YopP or TBP-PE38 cause death of activated primary macrophages, but unlike TBP-PE38, TBP-YopP is capable of inhibiting TNF secretion in activated primary macrophages.

Thus, TBP-YopP has the following desirable and specific effect oil activated macrophages, which can be exploited for therapeutical purposes: it decreases TNF-α production in macrophage cells without killing such cells.

Example 6

Inhibitory Effect of TBP-YopP on the Phosphorylation of p38 in HeLa M9 Cells

YopP protein is known to inhibit the MAPK and the NF-κB pathways. In the preceding Example it was shown that TBP-YopP has no cytophatic effect in HeLaM9 cells. In order to explore if there is any effect of TBP-YopP in HeLa M9 cells, phosphorylation of p38, indicative of signaling trough the MAPK cascade, was examined.

HeLa M9 (200,000 cells per well) was seeded in 96-wells plate and subjected to starvation for 16-18 hours in Fcs-free RPMI, containing Insulin, 1 mkg/ml, Transferrin, 1 µg/ml, Na Selenite, 1 ng/ml, Na Pyruvate, non-essential amino acids, glutamine. Then 1 µg of recombinant TBP-YopP in a volume of 10 µl was applied on the cells and allowed to interact with TNF on the cell surface and penetrate the cells for 1 h. For control 10 µl of solvent (50 mM Borate/NaOH Buffer, pH8.5) was added to the cells. Then, the cells were activated by 10% heat inactivated Fcs (HFcs) for different time intervals of time, from 60 to 5 min in presence of TBP-YopP as indicated on FIG. 11A, so that the total time of incubation with TBP-YopP for all the cells was 2 hours. Subsequently, the cells were lysed on ice in 50 µl of phosphate buffer in presence of phosphatase inhibitors: NaVa, 1 mM and NaF, 10 mM and proteases inhibitors: PMSF, 1 mM and complete (Roche). {Phosphate buffer: 50 mM NaH2PO4, 300 mM NaCl, 1% Triton, pH8.0}. The cell lysates were subjected to Western blot analysis detected with polyclonal antibody specific for phosphorylated p38 (pP38) (Cell Signalling). The same blots were re-probed with anti IKK-α (monoclonal anti-IKK-α, Santa Cruz) for normalization of protein loaded.

FIGS. 11B and C show the results of two experiments where cells were treated as indicated of FIG. 11A, or instead TBP-YopP, the solvent (Borate buffer) was used to compare p38 phosphorylation in the presence or in the absence of TBP-YopP In the results of two experiments (FIG. 11B and C) phosphorylation of p38 in HeLaM9 was observed after 5 minutes of HFcs activation. Phosphorylation increased in the first ten minutes and gradually decreased 30 and 60 minutes after HFcs activation. It was found that TBP-YopP inhibited phosphorylation of p38 in HeLaM9 cells, at least, up to 30 minutes after HFcs activation.

The results obtained in this experiment show that, although TBP-YopP was not cytotoxic for the epithelial cells HeLa M9 cells, it apparently penetrated HeLa M9 cells as manifested by TBP-YopP inhibitory action on the MAPK signaling cascade.

Example 7

Cells Expressing TNF on Their Surface

Two cell lines were used for exploring the effect of TBP-YopP: (a) the human acute monocytic leukemia THPI cells (obtained from the German Collection of Microorganisms and Cell Culture). Monocytic differentiation of these cells can be induced with phorbol myristate acetate (PMA). These cells are cultured at a cell density range of $0.3-1\times106/ml$ in RPMI 1640 medium supplemented with 10% Fcs, 2 mM L-glutamine, 1 mM Na-pyruvate, 1% nonessential amino acids. 9 mg/ml Insulin 100 mg/ml penicillin and 100 mg/ml streptomycin. To enhance cell surface TNT, expression, these cells, activated with PMA (for 16-20 hours, 100 ng/ml) were treated with LPS (1 mkg/ml for 1.5 h) and with 10 mcg/ml metalloprotease inhibitor GM6001 (Calbiochem) for two hours prior to tests.

(b) HeLa-M9 cells, a clone of the epithelial HeLa cervical carcinoma line that constitutively expresses under control of the SV40 promoter a human TNF mutant cDNA in which the arginine at position +2 and the serine at position +3 are substituted for threonines. These mutations cause an about tenfold reduction in the cleavage rate of 26 kDa TNF. The cells are cultured in RPMI 1640 medium supplemented with 10% Fcs, 2 mM L-glutamine, 100 mg/ml penicillin, 100 mg/l ml streptomycin and 50 mg/nl gentamycin.

TNF-expression on the cell surface of THPI cells was assessed by FACS in presence of inhibitor of metalloproteases GM6001, 10 µg/ml (Calbiochem) to prevent shedding of TNF-α. Samples of $5\times10^5$ cells were incubated in Fcs-free RPMI, containing Insuline, 1 mkg/ml, Transferrin, 1 µg/ml, Na Selenite, 1 ng/ml, Na Pyruvate, non-essential amino acids, glutamine with PMA 50-100 ng/ml for 16 h. Then LPS $E.\ coli$ 0111-B4 was added at concentration 1 µg/ml together with GM6001, 10 µg/ml for 2 h. For FACS analysis of TNF-expression on cell surface, cells were washed at 4 C in phosphate buffered saline (PBS) containing 2 mg/ml BSA, 0.1% sodium azide and incubated with FITC-anti-humanTNF antibodies. Analysis was performed by FACScan (Becton. Dickinson, Mountain View, Calif.). It was found that at least 30% of cells express TNF-α on their surface.

Example 8

Internalization Assay

TNF-α expressing cells (HeLa M9 or others) are labeled with $[^{125}I]$-conjugate (1 mcg/ml) at 37° C. in medium containing 0.1 mg/ml of BSA. The cells are then trypsinized and washed with ice-cold PBS, resuspended in 0.3% Pronase in PBS and left for 40 min at 2 C before centrifugation through dibutylphthalate. Endocytosis efficiency is expressed as the Pronase-resistant percentage of cell-associated $[^{125}I]$-conjugate after 30 min of uptake (modified from Taupiac M-P., et. Al, 1999).

Example 9

SDS-PAGE and Immunoblotting

Cells pellets collected by centrifugation are dissolved in Laemmli buffer. Samples are boiled for 5 minutes prior to application to a 0.1% SDS, 10% acrylamide slab gel. The gels can be stained by comassie blue or by silver staining.

For immunoblotting, samples after electrophoresis are transferred to a nitrocellulose paper, followed by reaction with antibody to the toxin or to the soluble form of the TNF receptor, then a second antibody linked to HRP (for the toxin-goat anti-rabbit antibody, for the soluble TNF receptor-goat anti mouse antibody) and staining. Known monoclonal antibodies against the soluble TNF receptors are employed as described (Engelmann et al., 1990 and Bigda et al., 1994).

Example 10

Therapeutic Activity of the Fusion Protein in a Murine Model for Spontaneous Development of Arthritis Transgenic mice expressing a human TNF transgene in which the 3' noncoding region, which provides translational regulation of its expression was expressed with that of the β-globin gene (Keffer et al., 1991) are used. Two weeks after birth, the mice are injected intraperitoneally with various doses of the test protein (the fusion protein and, as controls, of the toxin and of the soluble TNF receptor incorporated to the fusion protein) and then injected again once weekly for a period of 9 weeks. Swelling of the hind leg ankle joints of the mice are assessed periodically by determining the diameter of the joint. Lesions/alterations involving the joint structures: joint capsule, joint space, synovial membrane, articular cartilage, and subchondral bone are evaluated histologically.

Example 11

Therapeutic Activity of the Fusion Protein in a Murine Model for Antigen-induced Arthritis Lewis rats are immunized in the hind flank with 0.5 mg methylated bovine serum albumin (mBSA) in complete Freund's adjuvant. Twenty-one days later (day 0), the animals are injected in both hind knee joints with 50 µg mBSA in pyrogen-free saline. The rats are injected intra-articularly with the tested protein (the fusion protein and, as controls, of the toxin and of the soluble TNF receptor incorporated to the fusion protein) in both knee joints on that day and on the following 2 days (days 0, 1 and 2). Knee joint width is measured daily on days 0-6 relative to treatment. Histopathological examination of the joints harvested on day 6 is performed. Lesions/alterations involving the knee joint structures: joint capsule, joint space, synovial membrane, articular cartilage, and subchondral bone are evaluated.

Example 12

Therapeutic Activity of the Fusion Protein in a Murine Model for Antigen-induced Arthritis Male DBA/1 mice (8-12 weeks old) are immunized with 100 µg of type II collagen emulsified in FCA (Difco, Detroit, Mich.) by intradermal injection at the base of the tail. Starting from the time of immunization, the mice are injected intraperitoneally twice weekly with the test protein (the fusion protein and, as controls, of the toxin and of the soluble TNF receptor incorporated to the fusion protein) in PBS until onset of clinical arthritis. From day 15 after immunization mice are examined daily, for 10 days, for onset of disease using two clinical parameters: paw swelling and clinical score. Paw swelling is assessed by measuring the thickness of the first affected hind paw with calipers.

Example 13

Therapeutic Activity of the Fusion Protein in a Murine Model for of Colitis

IL-10 knockout mice, purchased in Harlan UK are interbred to generate mice homozygous for IL10 gene deletion and screened for homozygosity by PCR carried out on their tail DNA. Starting at the age of 4 weeks, the mice are injected intraperitoneally three times weekly with the test protein (the fusion protein and, as controls, of the toxin and of the soluble TNF receptor incorporated to the fusion protein) in PBS till the age of 20 weeks. The clinical score, histological analysis of the intestine and the content of inflammatory cytokines in the stools were evaluated as described in (Scheinin et al. 2003).

Example 14

Construction of a Plasmid for the Expression of a Conjugate of the Soluble Form of the p75 TNF Receptor The sequence of the soluble form of the p75 TNF receptor (TNFRSF1B, Genbank ID M32315) incorporated into the conjugate corresponds to the full sequence of the extracellular domain of the receptor (Leu 1 till Asp 235). This sequence is fused to that of the toxin and inserted into the pET-vector as described for example 1.

REFERENCES

Andreakos, E. T., et al., (2002) Cytokines and anti-cytokine biologicals in autoimmunity: present and future. Cytokine Growth Factor Rev 13(4-5): p. 299-313.

Asadullah K., et al., (2002) "Novel immunotherapies for psoriasis." Trends in Immunology, January, 23, N1, pp 47-53.

Belcher et al., (2000) "Activated monocytes in sickle cell disease: potential role in the activation of vascular endothelium and vaso-occlusion" Blood Vol. 96, No. 7, pp. 2451-2459.

Ben-Yehudah, A., et al., (2000) "Utilizing chimeric proteins for exploring the cellular fate of endogenous proteins." Biochem Biophys Res Commun, 2002. 290(1): p. 332-8.

Beutler, B. A., (1999) "The role of tumor necrosis factor in health and disease. J Rheumatol," 26 Suppl 57: p. 16-21.

Bigda, J., et al., (1994) "Dual role of the p75 tumor necrosis factor (TNF) receptor in TNF cytotoxicity." J Exp Med. 180 (2): p. 445-60.

Brinkmann, U. and Pastan I., (1995) "Recombinant Immunotoxins: From Basic Research to Cancer Therapy." Methods 8: p. 143-156.

Cornelis G R, Denecker G., (2001) "*Yersinia* lead SUMO attack." Nat Med. 7(1):21-3.

Engelmann, H., et al., (1990) "Antibodies to a soluble form of a tumor necrosis factor (TNF) receptor have TNF-like activity." J. Biol. Chem. 265(24): p. 14497-504.

Ghezzi P et al., (1998) "Tumor necrosis factor is increased in the spinal cord of an animal model of motor neuron degeneration." Eur Cytokine Netw. 9(2): 139-44.

Hongo et al., (2004) "Endogenous nitric oxide protects against T cell-dependent lethality during graft-versus-host disease and idiopathic pneumonia syndrome." J. Immunology, v. 173:1744-1756.

Jankovic, D. Z. Liu, and W. C. Gause. (2001) "Th1- and Th2-cell commitment during infectious disease: asymmetry in divergent pathways." Trends Immunol, 22(8): p. 450-7.

Kagi D., Ho A., et al., (1999) "TNF receptor 1-dependent beta cell toxicity as an effector pathway in autoimmune diabetes" J. Immunology 162:4598-4605.

Keffer, J., et al., (1991) "Transgenic mice expressing human tumour necrosis factor: a predictive genetic model of arthritis." EMBO J, 10(13): p. 4025-31.

Kollias, G., et al., (1999) "On the role of tumor necrosis factor and receptors in models of multiorgan failure, rheumatoid arthritis, multiple sclerosis and inflammatory bowel disease." Immunol Rev. 169: p. 175-94.

Locksley, R. M., N. Killeen, and M. J. Lenardo (2001) "The TNF and TNF receptor superfamilies: integrating mammalian biology." Cell 104(4): p. 487-501.

Lugering, A., et al., (2001) "Infliximab induces apoptosis in monocytes from patients with chronic active Crohn's disease by using a caspase-dependent pathway." Gastroenterology 121(5): p. 1145-57.

Mittler (2004) "Suppressing the self in rheumatoid arthritis." Nature medicine 10:10 pp 1047-49.

Nophar et al., (1990) "Soluble forms of tumor necrosis factor receptors (TNF-Rs). The cDNA for the type I TNF-R, cloned using amino acid sequence data of its soluble form, encodes both the cell surface and a soluble form of the receptor." EMBO J. (10):3269-78.

Orth et al., (1999) "Inhibition of the mitogen-activated protein kinase kinase superfamily by a *Yersinia* effector." Science 17;285(5435):1920-3.

Orth, (2002) "Function of the *Yersinia* effector YopJ." Curr Opin Microbiol. 5(1):38-43.

Prior et al., (1996) "Studies on the activity of Barnase Toxins in Vitro and in Vivo" Bioconjugate Chem., 7, 23-29.

Palmer et al., (1999) "YopJ of *Yersinia* spp. is sufficient to cause downregulation of multiple mitogen-activated protein kinases in eukaryotic cells," Infect Immun. 67(2):708-16.

Pacheco et al., (2002) "Reactive arthritis after BCG immunotherapy: T cell analysis in peripheral blood and synovial fluid" Rheumatology 41 pp 1119-1125.

Pastan. I., (2003) "Immunotoxins containing *Pseudomonas* exotoxin A: a short history." Cancer Immunol Immunother 52(5): p. 338-41.

Pastan, I. I. and Kreitman, R. J., (1998) "Immunotoxins for targeted cancer therapy." Adv Drug Deliv Rev. 31(1-2): p. 53-88.

Pocsik E, Duda E and Wallach D (1995) "Phosphorylation of the 26 kDa TNF precursor in monocytic cells and in transfected HeLa cells." J Inflammation, 45, 152-160.

Reimold, A. M., (2003) "New indications for treatment of chronic inflammation by TNF-alpha blockade." Am J Med Sci, 325(2): p. 75-92.

Ruckdeschel et al., (2001) "Arginine-143 of *Yersinia enterocolitica* YopP crucially determines isotype-related NF-kappaB suppression and apoptosis induction in macrophages" Infect Immun. 69(12):7652-62.

Scheinin, F. et al., (2003) "Validation of the interleukin-10 knockout mouse model of colitis: antitumour necrosis factor-antibodies suppress the progression of colitis." Clin Exp Immunol, 133(1): p. 38-43.

Siegall et al., (1989) "Functional analysis of domains II, Ib, and III of *Pseudomonas* exotoxin." J Biol Chem. August 25; 264(24):14256-61.

Singh J., Suruchi A (2004) "Antitnf-a strategy: Present status of this therapeutic paradigm" Indian J Pharmacol 36, 1, pp. 10-14.

Taupiac M P, Bebien M, Alami M, Beaumelle B., (1999) "A deletion within the translocation domain of *Pseudomonas* exotoxin A enhances translocation efficiency and cytotoxicity concomitantly." Mol Microbiol. 31(5):1385-93.

Van den Brande, J. M., et al., (2003) "Infliximab but not etanercept induces apoptosis in lamina propria T-lymphocytes from patients with Crohn's disease." Gastroenterology. 124(7): p. 1774-85.

Van Deventer, S. J., (2001) "Transmembrane TNF-alpha, induction of apoptosis, and the efficacy of TNF-targeting therapies in Crohn's disease." Gastroenterology 121(5): p. 1242-6.

Wallach, D., et al. (1999) "Tumor necrosis factor receptor and Fas signaling mechanisms." Annu Rev Immunol, 17: p. 331-67.

Wallach D, Arumugam T U, Boldin M P, Cantarella G, Ganesh K A, Goltsev Y, Goncharov T M, Kovalenko A V, Rajput A, Varfolomeev E E, Zhang S Q., (2002) "How are the regulators regulated? The search for mechanisms that impose specificity on induction of cell death and NF-kappaB activation by members of the TNF/NGF receptor family." Arthritis Res. 2002; 4 Suppl 3:S189-96.

The invention claimed is:

1. A chimeric protein comprising:
   the amino acid sequence of the extracellular portion of a TNF/NGF receptor, as a cell-specific targeting agent, and
   the amino acid sequence of a *Yersinia* outer protein P (YopP),
   which are connected by a polypeptide enabling translocation of the chimeric protein, from the endosome to the cytosol of a target cell, and
   wherein the chimeric protein has an inhibitory effect on TNF-mediated NF-κB activation.

2. The chimeric protein according to claim 1, wherein the extracellular portion of a TNF/NGF receptor is TNF binding protein 1 (TBP-1).

3. The chimeric protein according to claim 1, wherein the extracellular portion of a TNF/NGF receptor is TBP-2.

4. The chimeric protein according to claim 1, wherein YopP has reduced or non-apoptotic activity and is selected from YopP serogroups O: 3, O: 9 and O: 8 mutated in the Arginine-143 residue.

5. The chimeric protein according to claim 1, wherein the polypeptide enabling translocation includes the *Pseudomonas* exotoxin translocation domain or a fragment thereof.

6. The chimeric protein according to claim 5, wherein the fragment of the *Pseudomonas* exotoxin translocation domain is deficient in the last α-helix domain (F).

7. The chimeric protein according to claim 5, wherein the fragment of *Pseudomonas* exotoxin translocation domain, herein designated PEIItr, corresponds to the amino acid sequence of *Pseudomonas aeruginosa* exotoxin in FIG. 3 (SEQ ID NO: 3).

8. The chimeric protein according to claim 1, comprising one or two furin cleavage sites.

9. The chimeric protein according to claim 8, wherein one furin cleavage site is located at the N-terminus of the polypeptide enabling translocation, and one furin cleavage site is located at the N-terminus of the Yop protein.

10. The chimeric protein according to claim 8, wherein one furin cleavage site is the furin cleavage site of the Difteria toxin.

11. The chimeric protein according to claim 10, wherein the furin cleavage site has the amino acid sequence RVRR, herein designated DT.

12. The chimeric protein according to claim 11, wherein the chimeric protein consists of TBP-1, the translocation domain fragment of *Pseudomonas aeruginosa* exotoxin PEIltr, the furin cleavage site DT, and YopP, herein designated TBP-YopP, or salt thereof.

13. The chimeric protein according to claim 1, wherein the target cell is a lymphoid cell.

14. The chimeric protein according to claim 13, wherein the target cell is a macrophage.

15. The chimeric protein according to claim 13, wherein the target cell is a monocyte.

16. The chimeric protein according to claim 1, wherein the target cell is an epithelial cell.

17. A composition, comprising the chimeric protein according to claim 1 and a pharmaceutically acceptable carrier.

18. The composition according to claim 17, wherein the chimeric protein consists of a TNF binding protein 1 (TBP-1), a translocation domain fragment of *Pseudomonas aeruginosa* exotoxin PEIltr, a furin cleavage site DT, and YopP, herein designated TBP-YopP, or a mutein, variant, fusion protein, functional derivative, fragment, or salt thereof.

* * * * *